US007241807B2

(12) United States Patent
Xu et al.

(10) Patent No.: US 7,241,807 B2
(45) Date of Patent: Jul. 10, 2007

(54) PRODRUGS OF PROPOFOL, COMPOSITIONS AND USES THEREOF

(75) Inventors: Feng Xu, Palo Alto, CA (US); Mark A. Gallop, Los Altos, CA (US)

(73) Assignee: XenoPort, Inc., Santa Clara, CA (US)

( * ) Notice: Subject to any disclaimer, the term of this patent is extended or adjusted under 35 U.S.C. 154(b) by 76 days.

(21) Appl. No.: 11/180,332

(22) Filed: Jul. 12, 2005

(65) Prior Publication Data

US 2006/0041011 A1     Feb. 23, 2006

Related U.S. Application Data

(60) Provisional application No. 60/587,469, filed on Jul. 12, 2004.

(51) Int. Cl.
*A61K 31/265* (2006.01)
(52) U.S. Cl. .................................... 514/512; 558/248
(58) Field of Classification Search ............... 514/512; 558/248
See application file for complete search history.

(56) References Cited

U.S. PATENT DOCUMENTS

| | | | |
|---|---|---|---|
| 3,845,770 A | 11/1974 | Theeuwes et al. |
| 3,916,899 A | 11/1975 | Theeuwes et al. |
| 4,765,539 A | 8/1988 | Noakes et al. |
| 4,962,885 A | 10/1990 | Coffee |
| 5,112,598 A | 5/1992 | Biesalski |
| 5,556,611 A | 9/1996 | Biesalski |
| 5,698,155 A | 12/1997 | Grosswald et al. |
| 5,950,619 A | 9/1999 | van der Linden et al. |
| 5,954,047 A | 9/1999 | Armer et al. |
| 5,970,974 A | 10/1999 | van der Linden et al. |
| 6,254,853 B1 | 7/2001 | Hendler et al. |
| 6,362,234 B1 | 3/2002 | Hendler |
| 2001/0025035 A1 | 9/2001 | Stella et al. |

FOREIGN PATENT DOCUMENTS

| | | |
|---|---|---|
| WO | WO 94/12285 | 6/1994 |
| WO | WO 94/14543 | 7/1994 |
| WO | WO 95/26234 | 10/1995 |
| WO | WO 95/26235 | 10/1995 |
| WO | WO 95/32807 | 12/1995 |
| WO | WO 99/58555 | 11/1999 |
| WO | WO 9958555 A2 * | 11/1999 |
| WO | WO 00/48572 | 8/2000 |
| WO | WO 00/54588 | 9/2000 |
| WO | WO 01/20331 | 3/2001 |
| WO | WO 02/13810 | 2/2002 |
| WO | WO 2004/033424 | 4/2004 |

OTHER PUBLICATIONS

Adibi, "The oligopeptide transporter (Pept-1) in Human Intestine: Biology and Function," *Gastroenterology* 1997, 113, 332-340.

Alderman, "A Review of cellulose Ethers in Hydrophilic Matrices dor Oral controlled-Release Dosage Forms," *Int. J. Pharm. Tech. & Prod. Mfr.* 1984, 5(3) 1-9.

Anderson et al., "Alpha-amino acid phenolic ester derivatives: novel water-soluble general anesthetic agents which allosterically modulate GABA(A) receptors," *J. Med. Chem.* 2001, 44, 3582-3591.

Bamba et al., "Release Mechanisms in Gelforming Sustained Release Preparations," *Int. J. Pharm.* 1979, 2, 307.

Banaszczyk et al., "Propofol Phosphate, a Water-Soluble Propofol Prodrug: In Vivo Evaluation," *Anesth. Analg.* 2002, 95, 1285-1292.

Borgeat et al., "Preliminary Communication: Adjuvant Propofol Enables Better Control of Nausea and Emesid Secondary to Chemotherapy for Breast Cancer," *Can. J. Anaesth.* 1994, 41, 1117-1119.

Borgeat et al., "Propofol improves patient comfort during cisplatin chemotherapy. A pilot study," *Oncology* 1993, 50, 456-459.

Briggs et al., "An Adverse Rection to the Administration of Disoprofol (Diprvan)," *Anaesthesia* 1982, 37, 1099-1101.

Brooker at al., "Propofol Maintenance to Reduce Postoperatiove Emesis in Thyroidectomy Patients: A Group Sequential Comparison with Isoflurane/Nitrous Oxide," *Anaesth. Intensive Care* 1998, 26, 625-629.

Brown et al., "Role of Propofol in Refractory Status Epilepticus," *Pharmacother.* 1998, 32, 1053-1059.

De la Cruz et al., "The Effect of Propofol on Oxidative Stress in Platelets from Surgical Patients," *Anesth. Analg.* 1999, 89, 1050-1055.

During et al., "Controlled release of dopamine from a polymeric brain implant: in vivo characterization," 1989, *Ann. Neurol.* 25:351.

Gan et al., "Determination of Plasma Concentrations of Propofol Associated with 50% Reduction in Postoperative Nausea," *Anesthesiology.* 1997, 87, 779-784.

Hasan et al., "Comparison of the Effects of the Propofol and Thiopental on the Pattern of Maximal Electroshock Seizures in a Rat," *Pharmacol. Toxicol.* 1994, 74, 50-53.

Hashimoto et al., "Abnormal Activity in the Globus Pallidus in the Off-Period Dystonia," *Annals. of Neurology*, 2001, 49. 242-275.

Holtkamp et al., "Propofol in subanesthetic doses terminates status epilepticus in a rodent model," *Ann. Neurol.* 2001, 49, 260-263.

Howard et al., "Intercerebral Drug Delivery in Rats with Lesion-Induced Memory Deficits," 1989, *J. Neurosurg.* 71:105-112.

Krusz et al., "Intravenous Propofol: Unique Effectiveness in Treating Intractable Migraine," *Headache 2000*, 40, 224-230.

(Continued)

*Primary Examiner*—Kamal A. Saeed
*Assistant Examiner*—Joseph R. Kosack
(74) *Attorney, Agent, or Firm*—Dorsey & Whitney LLP; Timothy A. Worrall

(57) ABSTRACT

The present invention provides propofol prodrugs, methods of making propofol prodrugs, pharmaceutical compositions of propofol prodrugs and methods of using propofol prodrugs and pharmaceutical compositions thereof to treat or prevent diseases or disorders such as migraine headache pain and post-chemotherapy or post-operative surgery nausea and vomiting.

49 Claims, No Drawings

OTHER PUBLICATIONS

Kuisma et al., "Propofol in Prewhospital Treatment of Convulsive Status Epilepticus," *Epilepsia* 1995, 36, 1241-1243.

Langer et al., "Chemical and Physical Structure of Polymers as Carriers for Controlled Release of Bioactive Agents: A Review," *J Macromol. Sci. Rev. Macromol Chem.* 1983, 23:61.

Langley et al., "Propofol. A review of its pharmacodynamic and pharmacokinetic properties and use as an intravenous anaesthetic," *Drugs* 1988, 35, 334-372.

Leibach et al., "Peptide transporters in the intestine and the kidney," *Ann. Rev. Nutr.* 1996, 16, 99-119.

Levy et al., "Inhibition of Calcification of Bioprosthetic Heart Valves by Local Controlled-Release Diphosphonate," *Science* 1985 228: 190-192.

Murphy et al., "The Antioxideant Potential of Propofol (2,6-Diisopropylphenol)," *Br. J. Anaesth.* 1992, 68, 613-618.

Peduto et al., "Biochemical and Electrophysiologic Evidence that Propofol Enhances GABAergic Transmission in the Rat Brain," *Anesthesiology* 1991, 75, 1000-1009.

Phelps, et al., "Propofol in Chemotherapy-Associated Nausea and Vomiting," *Ann Pharmacother*, 1996, 30(3):290-292.

Picard, et al., "Prevention of Pain on Injection with Propofol: A Quantitative Systematic Review," *Anesth. Analg.*, 2000, 90:963-969.

Pop, et al., "Syntheses and Preliminary Pharmacological Evaluation of Some Chemical Delivery Systems of 2,6-diisopropylphenol (Propofol)," *Med. Chem. Res.*, 1992, 2(1):16-21.

Raleigh et al., "Searching for the Link Between Hypoxia and Poor Prognoses in Human Tumors," *Proc. Amer. Assoc. Cancer Research Annual Meeting*, 1999, 40, 397.

Raleigh et al., "Pharmacokinetics of Isotretinoin (ISO) in Rats Following Oral Dosing or Aerosol Inhalation," *British J. Cancer*, 1999, 80, Suppl. 2, 96-97.

Raoof, et al., "In Vivo Assessment of Intestinal, Hepatic, and Pulmonary First Pass Metobolism of Propofol in the Rat," *Pharm Res.* 1996, 13(6): 891-895.

Sagara, et al., "Propofol Hemisuccinate Protects Neuronal Cells from Oxidative Injury," *J Neurochem.*, 1999, 73(6):2524-2530.

Saudek et al., "A Preliminary Trial of the Programmable Implantable Medication System for Insulin Delivery," *N. Engl. J. Med.*, 1989, 321:574.

Sefton, "Implantable Pumps," *CRC Crit Ref Biomed. Eng.* 1987, 14:201-240.

Simonian, et al., "Oxidative Stress in Neurodegenerative Diseases," *Pharmacol. Toxicol.*, 1996, 36:83-106.

Sutherland et al., "Propofol and Seizures," *Anaesth. Intensive Care*, 1994, 22, 733-737.

Tomioka, et al., "Propofol is Effective in Chemotherapy-Induced Nausea and Vomiting: A Case Report with Quantitative Analysis," *Anesth. Analg.*, 1999, 89:798-799.

Tramer, et al., "Propofol anaesthesia and postoperative nausea and vomiting: quantitative systematic review of randomized controlled studies," *Br J Anasth*, 1997, 78:247-255.

Trapani et al., "Water-Soluble Salts of Aminoacid Esters of the Anaesthetic Agent Propofol," *Int. J. Pharm.* 1998, 175, 195-204.

Trapini, et al., "Propofol Analogues. Synthesis, Relationships between Structure and Affinity at $GABA_A$ Receptor in Rat Brain, and Differential Electrophysiological Profile at Recombinant Human $GABA_A$ Receptors," *J. Med. Chem.*, 1998, 41:1846-1854.

Verma et al., "Osmotically Controlled Oral Drug Delivery," *Drug Dev. Ind. Pharm.*, 2000, 26:695-708.

Walder et al., "Seizure-like phenomena and propofol: A systematic review," *Neurology* 2002, 58, 1327-1332.

Wang et al. "Propofol reduces infarct size and striatal dopamine accumulation following transient middle cerebral artery occlusion: a microdialysis study," *Eur. J. Pharmacol.* 2002, 452, 303-308.

Young et al., "Propofol neuroprotection in a rat model of ischaemia reperfusion injury," *Eur. J. Anaesthesiol.* 1997, 14, 320-326.

\* cited by examiner

PRODRUGS OF PROPOFOL, COMPOSITIONS AND USES THEREOF

This application claims the benefit under 35 U.S.C. § 119(e) from U.S. Provisional Application Ser. No. 60/587,469, filed Jul. 12, 2004 which is herein incorporated by reference in its entirety.

1. TECHNICAL FIELD

The present invention provides propofol prodrugs, methods of making propofol prodrugs, pharmaceutical compositions of propofol prodrugs and methods of using propofol prodrugs and pharmaceutical compositions thereof to treat or prevent diseases or disorders such as migraine headache pain and post-chemotherapy or post-operative surgery nausea and vomiting.

2. BACKGROUND ART

Propofol (2,6-diisopropylphenol), (1), is a low molecular weight phenol that is widely used as an intravenous sedative-hypnotic agent in the induction and maintenance of anesthesia and/or sedation in mammals. The advantages of propofol as an anesthetic include rapid onset of anesthesia, rapid clearance, and minimal side effects (Langley et al., *Drugs* 1988, 35, 334-372). Propofol may mediate hypnotic effects through interaction with the GABAA receptor complex, a hetero-oligomeric ligand-gated chloride ion channel (Peduto et al., *Anesthesiology* 1991, 75, 1000-1009).

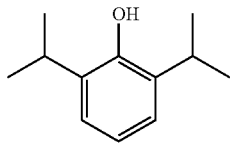

Propofol (1)

Propofol is rapidly metabolized in mammals with the drug being eliminated predominantly as glucuronidated and sulfated conjugates of propofol and 4-hydroxypropofol (Langley et al., *Drugs* 1988, 35, 334-372). Propofol clearance exceeds liver blood flow, which indicates that extrahepatic tissues contribute to the overall metabolism of the drug. Human intestinal mucosa glucuronidates propofol in vitro and oral dosing studies in rats indicate that approximately 90% of the administered drug undergoes first pass metabolism, with extraction by the intestinal mucosa accounting for the bulk of this presystemic elimination (Raoof et al., *Pharm. Res.* 1996, 13, 891-895). Because of its extensive first-pass metabolism, propofol is administered by injection or intravenous infusion and oral administration has not been considered therapeutically effective.

Propofol has a broad range of biological and medical applications, which are evident at sub-anesthetic doses and include treatment and/or prevention of intractable migraine headache pain (Krusz et al., *Headache* 2000, 40, 224-230; Krusz, International Publication No. WO 00/54588). Propofol, when used to maintain anesthesia, causes a lower incidence of post-operative nausea and vomiting ("PONV") compared to common inhalation anesthetic agents and numerous controlled clinical studies support the anti-emetic activity of propofol (Tramer et al., *Br. J. Anaesth.* 1997, 78, 247-255; Brooker et al., *Anaesth. Intensive Care* 1998, 26, 625-629; Gan et al., *Anesthesiology* 1997, 87, 779-784).

Propofol has also been shown to have anti-emetic activity when used in conjunction with chemotherapeutic compounds (Phelps et al., *Ann. Pharmacother.* 1996, 30, 290-292; Borgeat et al., *Oncology* 1993, 50, 456-459; Borgeat et al., *Can. J Anaesth.* 1994, 41, 1117-1119; Tomioka et al., *Anesth. Analg.* 1999, 89, 798-799). Nausea, retching and/or vomiting induced by a variety of chemotherapeutic agents (e.g., cisplatin, cyclophosphamide, 5-fluorouracil, methotrexate, anthracycline drugs, etc.) has been controlled by low-dose propofol infusion in patients refractory to prophylaxis with conventional anti-emetic drugs (e.g., serotonin antagonists and corticosteroids).

Propofol has also been used to treat patients with refractory status epilepticus (Brown et al., *Pharmacother.* 1998, 32, 1053-1059; Kuisma et al., *Epilepsia* 1995, 36, 1241-1243; Walder et al., *Neurology* 2002, 58, 1327-1332; Sutherland et al., *Anaesth. Intensive Care* 1994, 22, 733-737). Further, the anticonvulsant effects of propofol have also been demonstrated in rat efficacy models at sub-anesthetic doses (Holtkamp et al., *Ann. Neurol.* 2001, 49, 260-263; Hasan et al., *Pharmacol. Toxicol.* 1994, 74, 50-53).

Propofol has also been used as an antioxidant (Murphy et al., *Br. J. Anaesth.* 1992, 68, 613-618; Sagara et al., *J. Neurochem.* 1999, 73, 2524-2530; Young et al., *Eur. J. Anaesthesiol.* 1997, 14, 320-326; Wang et al. *Eur. J. Pharmacol.* 2002, 452, 303-308). Propofol, at doses typically used for surgical anesthesia, has observable antioxidant effects in humans (De la Cruz et al., *Anesth. Analg.* 1999, 89, 1050-1055). Pathogenesis or subsequent damage pathways in various neurodegenerative diseases involve reactive oxygen species and accordingly may be treated or prevented with antioxidants (Simonian et al., *Pharmacol. Toxicol.* 1996, 36, 83-106). Examples of specific neurodegenerative diseases which may be treated or prevented with antioxidants include, but are not limited to, Friedrich's disease, Parkinson's disease, Alzheimer's disease, Huntington's disease, amyotrophic lateral sclerosis ("ALS"), multiple sclerosis ("MS"), Pick disease, inflammatory diseases and diseases caused by inflammatory mediators such as tumor necrosis factor (TNF) and IL-1.

A significant problem with the formulation and use of propofol is poor water solubility. Accordingly, propofol must be specially formulated in aqueous media using solubilizers or emulsifiers (Briggs et al., *Anaesthesia* 1982, 37, 1099-1101). For example, in a current commercial product (Diprivan®, Astra-Zeneca) an oil-in-water emulsion (the emulsifier is the lecithin mixture Intralipid®), is used to formulate propofol (Picard et al., *Anesth. Analg.* 2000, 90, 963-969). Unfortunately, the oil-in-water emulsion formulation causes discomfort and pain at the site of injection.

One potential solution to the poor water solubility of propofol that avoids the use of additives, solubilizers or emulsifiers and the attendant injection site pain, is a water-soluble, stable propofol prodrug that is converted to propofol in vivo. (Hendler et al., International Publication No. WO 99/58555; Morimoto et al., International Publication No. WO 00/48572; Hendler et al., U.S. Pat. No. 6,254,853; Stella et al., United States Patent Application No. US2001/0025035; Hendler, U.S. Pat. No. 6,362,234; Hendler, International Publication No. WO 02/13810; Sagara et al., *J. Neurochem.* 1999, 73, 2524-2530; Banaszczyk et al., *Anesth. Analg.* 2002, 95, 1285-1292; Trapani et al., *Int. J. Pharm.* 1998, 175, 195-204; Trapani et al., *J. Med. Chem.* 1998, 41, 1846-1854; Anderson et al., *J. Med. Chem.* 2001, 44, 3582-3591; Pop et al., *Med. Chem. Res.* 1992, 2, 16-21). A significant problem with these existing propofol prodrugs is their high stability in vivo. This stability prevents release of therapeutically significant concentrations of propofol, particularly when the prodrug is orally administered.

Accordingly, there is a need for propofol prodrugs, which are sufficiently labile under physiological conditions to provide therapeutically effective concentrations of propofol, particularly, when the prodrug is orally administered.

3. SUMMARY

Disclosed herein are propofol prodrugs, methods of making propofol prodrugs, pharmaceutical compositions of propofol prodrugs and methods of using propofol prodrugs to treat or prevent diseases or disorders such as migraine headache pain, neurodegenerative disorders and post-chemotherapy or post-operative surgery nausea and vomiting which satisfies the above need. In some embodiments, prodrugs of propofol and pharmaceutical compositions thereof are orally administered. In other embodiments, prodrugs of propofol are translocated across the gastrointestinal mucosa via passive absorption.

In one aspect, a compound according to structural Formula (I) is provided:

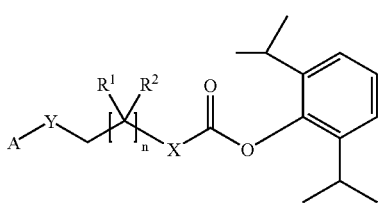

(I)

or pharmaceutically acceptable salts, hydrates, solvates or N-oxides thereof, wherein:

each $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^1$ and $R^2$ together with the carbon atom to which they are bonded form a cycloalkyl, substituted cycloalkyl, cycloheteroalkyl or substituted cycloheteroalkyl ring;

A is hydrogen, acyl, substituted acyl, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, A, Y and one of $R^1$ and $R^2$ together with the atoms to which they are bonded form a cycloheteroalkyl or substituted cycloheteroalkyl ring;

Y is —O— or —$NR^3$—;

$R^3$ is hydrogen, alkyl, substituted alkyl, arylalkyl or substituted arylalkyl;

n is an integer from 1 to 5;

X is —$NR^4$—, —O—, —$CH_2$— or —S—; and $R^4$ is hydrogen, alkyl, substituted alkyl, arylalkyl or substituted arylalkyl.

In another aspect, pharmaceutical compositions are provided. The pharmaceutical compositions disclosed herein generally comprise one or more compounds of Formulae (I)-(V) and (XII)-(XIV), and a pharmaceutically acceptable vehicle such as a diluent, carrier, excipient or adjuvant. The choice of diluent, carrier, excipient and adjuvant will depend upon, among other factors, the desired mode of administration. In some embodiments, the mode of administration is oral.

In still another aspect, methods for treating various diseases or disorders are provided. The methods disclosed herein generally comprise administering one or more compounds of Formulae (I)-(V) and (XII)-(XIV) in order to achieve a therapeutically effective concentration of propofol in the blood and/or tissue of a patient. The methods are useful for treating or preventing diseases or disorders including, but not limited to, migraine headache pain, post-chemotherapy or post-operative surgery nausea and vomiting and neurodegenerative disorders (e.g., epilepsy, Friedrich's disease, Parkinson's disease, Alzheimer's disease, Huntington's disease, amyotrophic lateral sclerosis (ALS), multiple sclerosis (MS), Pick disease, etc.). The methods generally involve administering to a patient in need of such treatment or prevention a therapeutically effective amount of one or more compounds of Formulae (I)-(V) and (XII)-(XIV), or a pharmaceutical composition containing one or more compounds of Formulae (I)-(V) and (XII)-(XIV).

In still another aspect, methods for inducing and/or maintaining anesthesia or sedation in a mammal are provided. The methods generally involve administering to a patient in need of such anesthesia or sedation induction and/or maintenance a therapeutically effective amount of one or more compounds of Formulae (I)-(V) and (XII)-(XIV), or a pharmaceutical composition containing one or more compounds of Formulae (I)-(V) and (XII)-(XIV).

4. DETAILED DESCRIPTION

4.1 Definitions

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms. "$C_{1-6}$ alkyl" refers to an alkyl group containing from 1 to 6 carbon atoms.

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, or heteroarylalkyl as defined herein. Representative examples include, but are not limited to formyl, acetyl, cyclohexylcarbonyl, cyclohexylmethylcarbonyl, benzoyl, benzylcarbonyl and the like.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms. In other embodiments, an aryl group comprises from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$). In other embodiments, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In some embodiments, the cycloalkyl group is (C$_3$-C$_{10}$) cycloalkyl. In other embodiments the cycloalkyl group is (C$_3$-C$_7$) cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{34}$R$^{35}$—, =N—N=, —N=N—, —N=N—NR$^{36}$R$^{37}$, —PR$^{38}$—, —P(O)$_2$—, —POR$^{39}$—, —O—P(O)$_2$—, —SO—, —SO$_2$—, —SnR$^{40}$R$^{41}$— and the like, where R$^{34}$, R$^{35}$, R$^{36}$, R$^{37}$, R$^{38}$, R$^{39}$, R$^{40}$ and R$^{41}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is from 5-20 membered heteroaryl. In other embodiments, the heteroaryl group is from 5-10 membered heteroaryl. In still other embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent refers to an acyclic alkyl radical in which one of the hydrogen atoms bonded to a carbon atom, typically a terminal or sp³ carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In other embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutically acceptable salt" refers to a salt of a compound of Formulae (I)-(V) and (XII)-(XIV), which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of Formulae (I)-(V) and (XII)-(XIV) is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl-containing drug may be converted to, for example, to an ester, carbonate, acyloxyalkyl or a sulfonate prodrug, which may be hydrolyzed in vivo to provide the hydroxyl compound. Prodrugs for drugs having functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, —M, —$R^{60}$, —O$^-$, =O, —O$R^{60}$, —S$R^{60}$, —S$^-$, =S, —N$R^{60}R^{61}$, =N$R^{60}$, —CF$_3$, —CN, —OCN, —SCN, —NO, —NO$_2$, =N$_2$, —N$_3$, —S(O)$_2$O$^-$, —S(O)$_2$OH, —S(O)$_2R^{60}$, —OS(O$_2$)O$^-$, —OS(O)$_2R^{60}$, —P(O)(O$^-$)$_2$, —P(O)(O$R^{60}$)(O—), —OP(O)(O$R^{60}$)(O$R^{61}$), —C(O)$R^{60}$, —C(S)$R^{60}$, —C(O)O$R^{60}$, —C(O)N$R^{60}R^{61}$, —C(O)O$^-$, —C(S)O$R^{60}$, —N$R^{62}$C(O)N$R^{60}R^{61}$, —N$R^{62}$C(S)N$R^{60}R^{61}$, —N$R^{62}$C(N$R^{63}$)N$R^{60}R^{61}$ and —C(N$R^{62}$)N$R^{60}R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring. In some embodiments, substituents include —M, —$R^{60}$, =O, —O$R^{60}$, —S$R^{60}$, —S⁻, =S, —N$R^{60}R^{61}$, =N$R^{60}$, —CF$_3$, —CN, —OCN, —SCN, —NO, —NO$_2$, =N$_2$, —N$_3$, —S(O)$_2R^{60}$, —OS(O$_2$)O⁻, —OS(O)$_2R^{60}$, —P(O)(O⁻)$_2$, —P(O)(O$R^{60}$)(O⁻), —OP(O)(O$R^{60}$)(O$R^{61}$), —C(O)$R^{60}$, —C(S)$R^{60}$, —C(O)O$R^{60}$, —C(O)N$R^{60}R^{61}$, —C(O)O⁻, —N$R^{62}$C(O)N$R^{60}R^{61}$. In other embodiments, substituents include —M, —$R^{60}$, =O, —O$R^{60}$, —S$R^{60}$, —N$R^{60}R^{61}$, —CF$_3$, —CN, —NO$_2$, —S(O)$_2R^{60}$, —P(O)(O$R^{60}$)(O⁻), —OP(O)(O$R^{60}$)(O$R^{61}$), —C(O)$R^{60}$, —C(O)O$R^{60}$, —C(O)N$R^{60}R^{61}$, —C(O)O⁻. In still other embodiments, substituents include —M, —$R^{60}$, —O$R^{60}$, —S$R^{60}$, —N$R^{60}R^{61}$—CF$_3$, —CN, —NO$_2$, —S(O)$_2R^{60}$, —OP(O)(O$R^{60}$)(O$R^{61}$), —C(O)$R^{60}$, —C(O)O$R^{60}$, —C(O)O⁻, where $R^{60}$, $R^{61}$ and $R^{62}$ are as defined above.

"Treating" or "treatment" of any disease or disorder refers to one or more of the following: (1) ameliorating the disease or disorder (i.e., arresting or reducing the development of the disease or at least one of the clinical symptoms thereof); (2) ameliorating at least one physical parameter, which may not be discernible by the patient; (3) inhibiting the disease or disorder, either physically, (e.g., stabilization of a discernible symptom), physiologically, (e.g., stabilization of a physical parameter), or both; and (4) delaying the onset of the disease or disorder.

"Therapeutically effective amount" means the amount of a compound or composition that, when administered to a patient, is sufficient to effect the desired therapy. The "therapeutically effective amount" will vary depending on the compound, the disease and its severity and the age, weight, etc., of the patient to be treated.

Reference will now be made in detail to certain compounds and methods of making and administering these compounds. The invention is not limited to those compounds and methods but rather is defined by the claim(s) issuing herefrom.

4.2 Compounds

The compounds disclosed herein are prodrugs of propofol. A first class of propofol prodrugs include compounds of structural Formula (I):

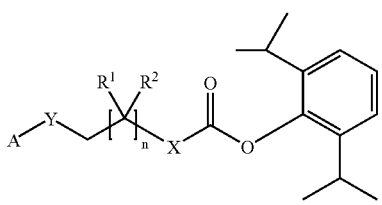

(I)

or pharmaceutically acceptable salts, hydrates, solvates or N-oxides thereof, wherein:

each $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^1$ and $R^2$ together with the carbon atom to which they are bonded form a cycloalkyl, substituted cycloalkyl, cycloheteroalkyl or substituted cycloheteroalkyl ring;

A is hydrogen, acyl, substituted acyl, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, A, Y and one of $R^1$ and $R^2$ together with the atoms to which they are bonded form a cycloheteroalkyl or substituted cycloheteroalkyl ring;

Y is —O— or —N$R^3$—;

$R^3$ is hydrogen, alkyl, substituted alkyl, arylalkyl or substituted arylalkyl;

n is an integer from 1 to 5;

X is —N$R^4$—, —O—, —CH$_2$— or —S—; and $R^4$ is hydrogen, alkyl, substituted alkyl, arylalkyl or substituted arylalkyl.

In some embodiments of compounds of Formula (I), X is —O— or —CH$_2$—. In other embodiments of compounds of Formula (I), X is —O— and Y is —NH— or —O—. In still other embodiments of compounds of Formula (I), X is —CH$_2$— and Y is —NH—.

In some embodiments of compounds of Formula (I), X is —O—, —NH— or —CH$_2$—. In other embodiments of compounds of Formula (I), Y is —O— or —NH—. In still other embodiments of compounds of Formula (I), X is —O— and Y is —NH— or —O—. In still other embodiments of compounds of Formula (I), X is —O—, —NH— or —CH$_2$—, and Y is —NH—.

In some embodiments of compounds of Formula (I), A is hydrogen or [H$_2$NCHR$^5$C(O)]—, and $R^5$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^5$ and the alpha amino group together with the atoms to which they are bonded form a cycloheteroalkyl or substituted cycloheteroalkyl ring.

In still other embodiments of compounds of Formula (I), A is hydrogen or [H$_2$NCHR$^5$C(O)]—, and $R^5$ is hydrogen, $C_{1-6}$ alkyl, substituted $C_{1-6}$ alkyl, $C_{5-7}$ aryl, substituted $C_{5-7}$ aryl, $C_{6-11}$ arylalkyl, substituted $C_{6-11}$ arylalkyl, $C_{1-6}$ heteroalkyl, substituted $C_{1-6}$ heteroalkyl, $C_{5-7}$ heteroaryl, substituted $C_{5-7}$ heteroaryl, $C_{6-11}$ heteroarylalkyl, substituted $C_{6-11}$ heteroarylalkyl or optionally, $R^5$ and the alpha amino group together with the atoms to which they are bonded form a $C_{5-7}$ cycloheteroalkyl or substituted $C_{5-7}$ cycloheteroalkyl ring.

In still other embodiments of compounds of Formula (I), A is hydrogen or [H$_2$NCHR$^5$C(O)]— and $R^5$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl.

In still other embodiments of compounds of Formula (I), A is hydrogen or [H$_2$NCHR$^5$C(O)]—, and $R^5$ is hydrogen, methyl, isopropyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$(CH$_2$)$_3$NH$_2$, 4-hydroxybenzyl, 3-indolylmethyl or $R^5$ and the alpha amino group together with the atoms to which they are bonded form a pyrrolidine ring.

In some embodiments of compounds of Formula (I), n is 1. In other embodiments of compounds of Formula (I), n is 2 or 3.

In some embodiments of compounds of Formula (I), each $R^1$ and $R^2$ is independently hydrogen, alkyl, substituted alkyl, arylalkyl, substituted arylalkyl or optionally, $R^1$ and $R^2$ together with the carbon atom to which they are bonded form a cycloalkyl or substituted cycloalkyl ring. In other embodiments of compounds of Formula (I), each $R^1$ and $R^2$ are independently hydrogen, alkyl or optionally, $R^1$ and $R^2$ together with the carbon atom to which they are bonded form a cycloalkyl ring, and preferably, $R^1$ and $R^2$ are each hydrogen, each methyl or $R^1$ and $R^2$ together with the carbon atom to which they are bonded form a cyclohexyl ring.

In some embodiments of compounds of Formula (I), each $R^1$ and $R^2$ is independently hydrogen, $C_{1-6}$ alkyl, substituted $C_{1-6}$ alkyl, or optionally, $R^1$ and $R^2$ together with the carbon atom to which they are bonded form a $C_{5-7}$ cycloalkyl or substituted $C_{5-7}$ cycloalkyl ring.

In some embodiments of compounds of Formula (I), the substituent is halogen, $-NH_2$, $-OH$, $-CN$, $-COOH$, $-C(O)NH_2$, $-C(O)OR^7$ or $-NR^7_3{}^+$ and each $R^7$ is independently $C_{1-3}$ alkyl.

In some embodiments of compounds of Formula (I), n is 1, Y is $-O-$ or $-NH-$, X is $-O-$, $-NH-$ or $-CH_2-$, $R^1$ and $R^2$ are each hydrogen, each methyl or $R^1$ and $R^2$ together with the carbon atom to which they are bonded from a cyclohexyl ring, and A is hydrogen or $[H_2NCHR^5C(O)]-$, wherein $R^5$ is hydrogen, methyl, isopropyl, $-CH_2OH$, $CH(OH)CH_3$, $-CH_2NH_2$, $-CH_2CO_2H$, $-CH_2CH_2CO_2H$, $-CH_2CONH_2$, $-CH_2(CH_2)_3NH_2$, 4-hydroxybenzyl, 3-indolylmethyl or $R^5$ and the alpha amino group together with the atoms to which they are bonded from a pyrrolidine ring.

In some embodiments, a compound according to structural Formula (H) is provided:

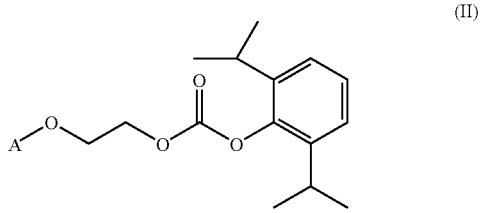

(II)

or pharmaceutically acceptable salts, hydrates, solvates or N-oxides thereof, wherein:

A is hydrogen or $[H_2NCHR^5C(O)]-$, and $R^5$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^5$ and the alpha amino group together with the atoms to which they are bonded form a cycloheteroalkyl or substituted cycloheteroalkyl ring.

In some embodiments of compounds of Formula (II), A is hydrogen or $[H_2NCHR^5C(O)]-$ and $R^5$ is hydrogen, $C_{1-6}$ alkyl, substituted $C_{1-6}$ alkyl, $C_{5-7}$ aryl, substituted $C_{5-7}$ aryl, $C_{6-11}$ arylalkyl, substituted $C_{6-11}$ arylalkyl, $C_{1-6}$ heteroalkyl, substituted $C_{1-6}$ heteroalkyl, $C_{5-7}$ heteroaryl, substituted $C_{5-7}$ heteroaryl, $C_{6-11}$ heteroarylalkyl, substituted $C_{6-11}$ heteroarylalkyl or optionally, $R^5$ and the alpha amino group together with the atoms to which they are bonded form a $C_{5-7}$ cycloheteroalkyl or substituted $C_{5-7}$ cycloheteroalkyl ring.

In some embodiments of compounds of Formula (II), the substituent is halogen, $-NH_2$, $-OH$, $-CN$, $-COOH$, $-C(O)NH_2$, $-C(O)OR^7$ or $-NR^7_3{}^+$ and each $R^7$ is independently $C_{1-3}$ alkyl.

In some embodiments of compounds of Formula (II), A is hydrogen or $[H_2NCHR^5C(O)]-$ and $R^5$ is hydrogen, methyl, isopropyl, isobutyl, sec-butyl, tert-butyl, cyclopentyl, cyclohexyl, $-CH_2OH$, $-CH(OH)CH_3$, $-CH_2CO_2H$, $-CH_2CH_2CO_2H$, $-CH_2CONH_2$, $-CH_2CH_2CONH_2$, $-CH_2CH_2SCH_3$, $-CH_2SH$, $-CH_2(CH_2)_3NH_2$, $-CH_2CH_2CH_2NHC(NH)NH_2$, phenyl, benzyl, 4-hydroxybenzyl, 4-imidazolylmethyl or 3-indolylmethyl.

In some embodiments of compounds of Formula (II), A is hydrogen or $[H_2NCHR^5C(O)]-$ and $R^5$ is $-CH_2OH$ or $-CH_2CONH_2$.

In some embodiments, a compound according to structural Formula (III) is provided:

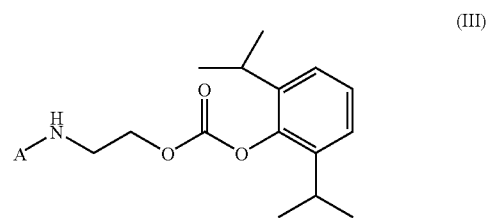

(III)

or pharmaceutically acceptable salts, hydrates, solvates or N-oxides thereof, wherein:

A is hydrogen, $[H_2NCHR^5C(O)]-$ or $-C(O)OR^6$;

$R^5$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^5$ and the alpha amino group together with the atoms to which they are bonded form a cycloheteroalkyl or substituted cycloheteroalkyl ring; and $R^6$ is alkyl, substituted alkyl, aryl, substituted aryl, arylalkyl or substituted arylalkyl.

In some embodiments of compounds of Formula (III), $R^5$ is hydrogen, $C_{1-6}$ alkyl, substituted $C_{1-4}$ alkyl, $C_{5-7}$ aryl, substituted $C_{5-7}$ aryl, $C_{6-11}$ arylalkyl, substituted $C_{6-11}$ arylalkyl, $C_{1-6}$ heteroalkyl, substituted $C_{1-4}$ heteroalkyl, $C_{5-7}$ heteroaryl, substituted $C_{5-7}$ heteroaryl, $C_{6-11}$ heteroarylalkyl, substituted $C_{6-11}$ heteroarylalkyl or optionally, $R^5$ and the alpha amino group together with the atoms to which they are bonded form a $C_{5-7}$ cycloheteroalkyl or substituted $C_{5-7}$ cycloheteroalkyl ring; and In some embodiments of compounds of Formula (III), $R^6$ is hydrogen, $C_{1-6}$ alkyl, substituted $C_{1-6}$ alkyl, $C_{5-7}$ aryl, substituted $C_{5-7}$ aryl, $C_{6-8}$ arylalkyl or substituted $C_{6-8}$ arylalkyl.

In some embodiments of compounds of Formula (III), the substituent is halogen, $-NH_2$, $-OH$, $-CN$, $-COOH$, $-C(O)NH_2$, $-C(O)OR^7$ or $-NR^7_3{}^+$ and each $R^7$ is independently $C_{1-3}$ alkyl.

In some embodiments of compounds of Formula (III), A is hydrogen or $[H_2NCHR^5C(O)-$, wherein $R^5$ is hydrogen, methyl, isopropyl, isobutyl, sec-butyl, tert-butyl, cyclopentyl, cyclohexyl, $-CH_2OH$, $-CH(OH)CH_3$, $-CH_2CO_2H$, $-CH_2CH_2CO_2H$, $-CH_2CONH_2$, $-CH_2CH_2CONH_2$, $-CH_2CH_2SCH_3$, $-CH_2SH$, $-CH_2(CH_2)_3NH_2$, $-CH_2CH_2CH_2NHC(NH)NH_2$, phenyl, benzyl, 4-hydroxybenzyl, 4-imidazolylmethyl or 3-indolylmethyl. In other embodiments of compounds of Formula (III), A is hydrogen or $[H_2NCHR^5C(O)]-$ and $R^5$ is hydrogen, isopropyl, $-CH_2OH$, $-CH_2CONH_2$, $-CH_2(CH_2)_3NH_2$ or 4-hydroxybenzyl. In still other embodiments of compounds of Formula (III), A is $-C(O)OR^6$ and $R^6$ is alkyl, aryl or arylalkyl. In still other embodiments, A is $-C(O)OR^6$ and $R^6$ is methyl, ethyl, tert-butyl or benzyl.

In some embodiments, a compound according to structural Formula (IV) is provided:

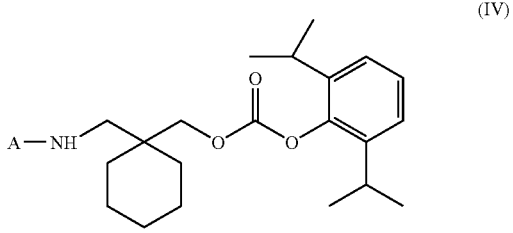

(IV)

or pharmaceutically acceptable salts, hydrates, solvates or N-oxides thereof, wherein:

A is hydrogen or [$H_2NCHR^5C(O)$]—, and $R^5$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^5$ and the alpha amino group together with the atoms to which they are bonded form a cycloheteroalkyl or substituted cycloheteroalkyl ring.

In some embodiments of compounds of Formula (IV), A is hydrogen or [$H_2NCHR^5C(O)$]— and $R^5$ is hydrogen, $C_{1-6}$ alkyl, substituted $C_{1-6}$ alkyl, $C_{5-7}$ aryl, substituted $C_{5-7}$ aryl, $C_{6-11}$ arylalkyl, substituted $C_{6-11}$ arylalkyl, $C_{1-6}$ heteroalkyl, substituted $C_{1-6}$ heteroalkyl, $C_{5-7}$ heteroaryl, substituted $C_{5-7}$ heteroaryl, $C_{6-11}$ heteroarylalkyl, substituted $C_{6-11}$ heteroarylalkyl or optionally, $R^5$ and the alpha amino group together with the atoms to which they are bonded form a $C_{5-7}$ cycloheteroalkyl or substituted $C_{5-7}$ cycloheteroalkyl ring.

In some embodiments of compounds of Formula (IV), the substituent is halogen, —$NH_2$, —OH, —CN, —COOH, —$C(O)NH_2$, —$C(O)OR^7$ or —$NR^7_3{}^+$ and each $R^7$ is independently $C_{1-3}$ alkyl.

In some embodiments of compounds of Formula (IV), A is hydrogen or [$H_2NCHR^5C(O)$]—, and $R^5$ is hydrogen, methyl, isopropyl, isobutyl, sec-butyl, tert-butyl, cyclopentyl, cyclohexyl, —$CH_2OH$, —$CH(OH)CH_3$, —$CH_2CO_2H$, —$CH_2CH_2CO_2H$, —$CH_2CONH_2$, —$CH_2CH_2CONH_2$, —$CH_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl or 3-indolylmethyl. In other embodiments of compounds of Formula (IV), A is [$H_2NCHR^5C(O)$]—, and $R^5$ is isopropyl, —$CH_2OH$ or —$CH(OH)CH_3$.

In some embodiments, a compound according to structural Formula (V) is provided:

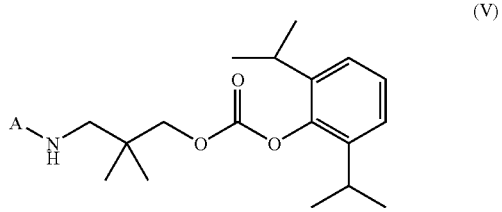

(V)

or pharmaceutically acceptable salts, hydrates, solvates or N-oxides thereof, wherein:

A is hydrogen or [$H_2NCHR^5C(O)$]—, and $R^5$ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^5$ and the alpha amino group together with the atoms to which they are bonded form a cycloheteroalkyl or substituted cycloheteroalkyl ring.

In some embodiments of compounds of Formula (V), A is hydrogen or [$H_2NCHR^5C(O)$]— and $R^5$ is hydrogen, $C_{1-6}$ alkyl, substituted $C_{1-6}$ alkyl, $C_{5-7}$ aryl, substituted $C_{5-7}$ aryl, $C_{6-11}$ arylalkyl, substituted $C_{6-11}$ arylalkyl, $C_{1-6}$ heteroalkyl, substituted $C_{1-6}$ heteroalkyl, $C_{5-7}$ heteroaryl, substituted $C_{5-7}$ heteroaryl, $C_{6-11}$ heteroarylalkyl, substituted $C_{6-11}$ heteroarylalkyl or optionally, $R^5$ and the alpha amino group together with the atoms to which they are bonded form a $C_{5-7}$ cycloheteroalkyl or substituted $C_{5-7}$ cycloheteroalkyl ring.

In some embodiments of compounds of Formula (V), the substituent is halogen, —$NH_2$, —OH, —CN, —OOH, —$C(O)NH_2$, —$C(O)OR^7$ or —$NR^7_3{}^+$ and each $R^7$ is independently $C_{1-3}$ alkyl.

In some embodiments of compounds of Formula (V), A is hydrogen or [$H_2NCHR^5C(O)$]—, and $R^5$ is hydrogen, methyl, isopropyl, isobutyl, sec-butyl, tert-butyl, cyclopentyl, cyclohexyl, —$CH_2OH$, —$CH(OH)CH_3$, —$CH_2NH_2$, —$CH_2CO_2H$, —$CH_2CH_2CO_2H$, —$CH_2CONH_2$, —$H_2CH_2CONH_2$, —$H_2CH_2SCH_3$, —$CH_2SH$, —$CH_2(CH_2)_3NH_2$, —$CH_2CH_2CH_2NHC(NH)NH_2$, phenyl, benzyl, 4-hydroxybenzyl, 4-imidazolylmethyl or 3-indolylmethyl. In other embodiments of compounds of Formula (V), A is [$H_2NCHR^5C(O)$]—, and $R^5$ is hydrogen, methyl, isopropyl, —$CH_2OH$, —$CH(OH)CH_3$, —$CH_2NH_2$, —$CH_2CO_2H$, —$CH_2CH_2CO_2H$, —$CH_2CONH_2$, —$CH_2CH_2SCH_3$, —$CH_2SH$, —$CH_2(CH_2)_3N$—$H_2$, 4-hydroxybenzyl or 3-indolylmethyl. In still other embodiments of compounds of Formula (V), A is [$H_2NCHR^5C(O)$]—, and $R^5$ and the alpha amino group together with the atoms to which they are bonded form a pyrrolidine ring.

In some embodiments, a compound according to structural Formula (XII) is provided:

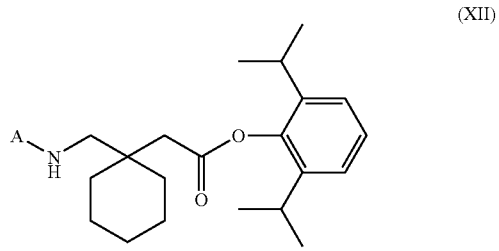

(XII)

or pharmaceutically acceptable salts, hydrates, solvates or N-oxides thereof, wherein:

A is hydrogen or [$H_2NCHR^5C(O)$]— and $R^5$ is hydrogen, $C_{1-6}$ alkyl, substituted $C_{1-6}$ alkyl, $C_{5-7}$ aryl, substituted $C_{5-7}$ aryl, $C_{6-11}$ arylalkyl, substituted $C_{6-11}$ arylalkyl, $C_{1-6}$ heteroalkyl, substituted $C_{1-6}$ heteroalkyl, $C_{5-7}$ heteroaryl, substituted $C_{5-7}$ heteroaryl, $C_{6-11}$ heteroarylalkyl, substituted $C_{6-11}$ heteroarylalkyl or optionally, $R^5$ and the alpha amino group together with the atoms to which they are bonded form a $C_{5-7}$ cycloheteroalkyl or substituted $C_{5-7}$ cycloheteroalkyl ring.

In some embodiments of compounds of Formula (XII), the substituent is halogen, —$NH_2$, —OH, —CN, —COOH, —$C(O)NH_2$, —$C(O)OR^7$ or —$NR^7_3{}^+$ and each $R^7$ is independently $C_{1-3}$ alkyl.

In some embodiments of compounds of Formula (XII), A is hydrogen or [$H_2NCHR^5C(O)$]— and $R^5$ is hydrogen, methyl, isopropyl, isobutyl, sec-butyl, tert-butyl, cyclopentyl, cyclohexyl, $H_2OH$, —$CH(OH)CH_3$, —$CH_2CO_2H$, —$H_2CH_2CO_2H$, —$CH_2CONH_2$, —$CH_2CH_2CONH_2$, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl or 3-indolylmethyl.

In some embodiments of compounds of Formula (XII), A is [H₂NCHR⁵C(O)]— and R⁵ is isopropyl, —H₂OH or —CH(OH)CH₃.

In some embodiments, a compound according to structural Formula (XIII) is provided:

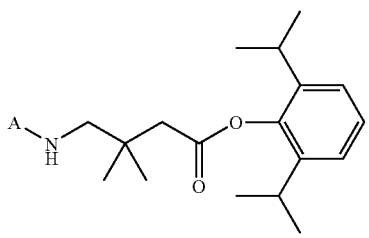

(XIII)

or pharmaceutically acceptable salts, hydrates, solvates or N-oxides thereof, wherein:

A is hydrogen or [H₂NCHR⁵C(O)]— and R⁵ is hydrogen, C₁₋₆ alkyl, substituted C₁₋₆ alkyl, C₅₋₇ aryl, substituted C₅₋₇ aryl, C₆₋₁₁ arylalkyl, substituted C₆₋₁₁ arylalkyl, C₁₋₆ heteroalkyl, substituted C₁₋₆ heteroalkyl, C₅₋₇ heteroaryl, substituted C₅₋₇ heteroaryl, C₆₋₁₁ heteroarylalkyl, substituted C₆₋₁₁ heteroarylalkyl or optionally, R⁵ and the alpha amino group together with the atoms to which they are bonded form a C₅₋₇ cycloheteroalkyl or substituted C₅₋₇ cycloheteroalkyl ring.

In other embodiments of compounds of Formula (XIII), the substituent is halogen, —NH₂, —OH, —N, POOH, —C(O)NH₂, C(O)OR⁷ or —NR⁷₃⁺ and each R⁷ is independently C₁₋₃ alkyl.

In other embodiments of compounds of Formula (XIII), A is hydrogen or [H₂NCHR⁵C(O)]— and R⁵ is hydrogen, methyl, isopropyl, isobutyl, sec-butyl, tert-butyl, cyclopentyl, cyclohexyl, —CH₂OH, —CH(OH)CH₃, —CH₂NH₂, —CH₂CO₂H, —CH₂CH₂CO₂H, —CH₂CONH₂, —CH₂CH₂CONH₂, —CH₂CH₂SCH₃, —CH₂SH, —CH₂(CH₂)₃NH₂, —CH₂CH₂CH₂NHC(NH)NH₂, phenyl, benzyl, 4-hydroxybenzyl, 4-imidazolylmethyl 3-indolylmethyl or R⁵ and the alpha amino group together with the atoms to which they are bonded form a pyrrolidine ring. In other embodiments of compounds of Formula (XIII), A is [H₂NCHR⁵C(O)]— and R⁵ is hydrogen, methyl, isopropyl, —CH₂OH, —CH(OH)CH₃, —CH₂NH₂, —CH₂CO₂H, —CH₂CH₂CO₂H, —CH₂CONH₂, —CH₂(CH₂)₃NH₂, 4-hydroxybenzyl, or R⁵ and the alpha amino group together with the atoms to which they are bonded form a pyrrolidine ring.

In some embodiments, a compound according to structural Formula (XIV) is provided:

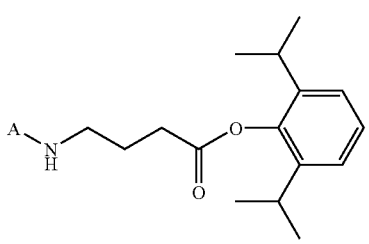

(XIV)

or pharmaceutically acceptable salts, hydrates, solvates or N-oxides thereof, wherein:

A is hydrogen or [H₂NCHR⁵C(O)]— wherein R⁵ is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, R⁵ and the alpha amino group together with the atoms to which they are bonded form a cycloheteroalkyl or substituted cycloheteroalkyl ring.

In some embodiments of compounds of Formula (XIV), A is hydrogen or [H₂NCHR⁵C(O)]— and R⁵ is hydrogen, C₁₋₆ alkyl, substituted C₁₋₆ alkyl, C₅₋₇ aryl, substituted C₅₋₇ aryl, C₆₋₁₁ arylalkyl, substituted C₆₋₁₁ arylalkyl, C₁₋₆ heteroalkyl, substituted C₁₋₆ heteroalkyl, C₅₋₇ heteroaryl, substituted C₅₋₇ heteroaryl, C₆₋₁₁ heteroarylalkyl, substituted C₆₋₁₁ heteroarylalkyl or optionally, R⁵ and the alpha amino group together with the atoms to which they are bonded form a C₅₋₇ cycloheteroalkyl or substituted C₅₋₇ cycloheteroalkyl ring.

In some embodiments of compounds of Formula (XIV), the substituent is halogen, —NH₂, —OH, —CN, —COOH, —C(O)NH₂, —C(O)OR⁷ or —NR⁷₃⁺ and each R⁷ is independently C₁₋₃ alkyl.

In some embodiments of compounds of Formula (XIV), A is hydrogen or [H₂NCHR⁵C(O)]— and R⁵ is hydrogen, methyl, isopropyl, isobutyl, sec-butyl, tert-butyl, cyclopentyl, cyclohexyl, —CH₂OH, —CH(OH)CH₃, —CH₂NH₂, —CH₂CO₂H, —CH₂CH₂CO₂H, —CH₂CONH₂, —CH₂CH₂CONH₂, —CH₂CH₂SCH₃, —H₂SH, —H₂(CH₂)₃ NH₂, —CH₂CH₂CH₂NHC(NH)NH₂, phenyl, benzyl, 4-hydroxybenzyl, 4-imidazolylmethyl 3-indolylmethyl or R⁵ and the alpha amino group together with the atoms to which they are bonded form a pyrrolidine ring. In other embodiments of compounds of Formula (XIV), A is [H₂NCHR⁵C(O)]— and R⁵ is —CH₂OH, —CH(OH)CH₃, —CH₂CH₂CO₂H, —CH₂CONH₂ or R⁵ and the alpha amino group together with the atoms to which they are bonded form a pyrrolidine ring.

In some embodiments of compounds of Formula (I), the compound is:

2,6-(Diisopropyl)phenyl 1-[((2S)-2-amino-3-methylbutyryl)aminomethyl]-1-cyclohexane acetate;

2,6-(Diisopropyl)phenyl 1-[((2S)-2-amino-3-hydroxypropionyl)aminomethyl]-1-cyclohexane acetate;

2,6-(Diisopropyl)phenyl 1-[((2S)-2-amino-(3R)-3-hydroxybutyryl)aminomethyl]-1-cyclohexane acetate;

2,6-(Diisopropyl)phenyl 4-[(2S)-2-amino-3-carbamoylpropionylamino]-3,3-dimethylbutanoate;

2,6-(Diisopropyl)phenyl 4-[(2S)-2-amino-3-carboxypropionylamino]-3,3-dimethylbutanoate;

2,6-(Diisopropyl)phenyl 4-[(2S)-2,3-diaminopropionylamino]-3,3-dimethylbutanoate;

2,6-(Diisopropyl)phenyl 4-[(2S)-2-amino-3-hydroxypropionylamino]-3,3-dimethylbutanoate;

2,6-(Diisopropyl)phenyl 4-[(2S)-2-aminopropionylamino]-3,3-dimethylbutanoate;

2,6-(Diisopropyl)phenyl 4-[(2S)-2-amino-(3R)-3-hydroxybutyryl]amino-3,3-dimethylbutanoate;

2,6-(Diisopropyl)phenyl 4-[(2S)-2-amino-(4-hydroxyphenyl)propionylamino]-3,3-dimethylbutanoate;

2,6-(Diisopropyl)phenyl 4-[(2S)-2-amino-(indol-3-yl) propionylamino]-3,3-dimethylbutanoate;

2,6-(Diisopropyl)phenyl 4-[aminomethylcarbonylamino]-3,3-dimethylbutanoate;

2,6-(Diisopropyl)phenyl 4-[(2S)-2-amino-4-carboxybutyrylamino]-3,3-dimethylbutanoate;

2,6-(Diisopropyl)phenyl 4-[(2S)-2,6-diaminohexanoylamino]-3,3-dimethylbutanoate;

2,6-(Diisopropyl)phenyl 4-[(2S)-pyrrolidin-2-ylcarbonylamino]-3,3-dimethylbutanoate;

2,6-(Diisopropyl)phenyl 4-[(2S)-2-amino-3-methylbutyrylamino]-3,3-dimethylbutanoate;

2-[2,6-(Diisopropyl)phenoxycarbonyloxy]ethyl (2S)-2-amino-3-carbamoylpropionate;

2-[2,6-(Diisopropyl)phenoxycarbonyloxy]ethanol 2-[2,6-(Diisopropyl)phenoxycarbonyloxy]ethyl (2S)-2-amino-3-hydroxypropionate;

2-[2,6-(Diisopropyl)phenoxycarbonyloxy]ethyl (2S)-2-amino-3-carbamoylpropionamide;

1-Amino-2-[2,6-(diisopropyl)phenoxycarbonyloxy]ethane;

2-[2,6-(Diisopropyl)phenoxycarbonyloxy]ethyl glycinamide;

2-[2,6-(Diisopropyl)phenoxycarbonyloxy]ethyl (2S)-2,6-diaminohexanoylamide;

2-[2,6-(Diisopropyl)phenoxycarbonyloxy]ethyl (2S)-2-amino-3-hydroxypropionamide;

2-[2,6-(Diisopropyl)phenoxycarbonyloxy]ethyl (2S)-2-amino-(4-hydroxyphenyl)propionamide;

2-[2,6-(Diisopropyl)phenoxycarbonylamino]ethyl (2S)-2-amino-3-carboxypropionamide;

2-[2,6-(Diisopropyl)phenoxycarbonylamino]ethyl (2S)-2-amino-3-hydroxypropionamide;

2-[2,6-(Diisopropyl)phenoxycarbonylamino]ethyl (2S)-2-amino-3-methylbutanoylamide;

2,6-(Diisopropyl)phenyl 4-[(2S)-2-amino-3-methylbutyrylamino]butanoate;

2,6-(Diisopropyl)phenyl 4-[(2S)-2-amino-3-carbamoylpropionylamino]butanoate;

2,6-(Diisopropyl)phenyl 4-[(2S)-2-amino-4-carboxybutyrylamino]butanoate;

2,6-(Diisopropyl)phenyl 4-[(2S)-2-amino-(3R)-3-hydroxybutyryl]aminobutanoate;

2,6-(Diisopropyl)phenyl 4-[(2S)-pyrrolidin-2-ylcarbonylamino]butanoate;

2,6-(Diisopropyl)phenyl 4-[(2S)-2-amino-3-hydroxypropionylamino]butanoate;

or pharmaceutically acceptable salts, hydrates, solvates or N-oxides thereof.

Compounds disclosed herein may be identified either by their chemical structure and/or chemical name. If the chemical structure and chemical name conflict, the chemical structure is determinative of the identity of the compound.

Compounds described herein may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Compounds disclosed herein may also exist in several tautomeric forms including the enol form, the keto form and mixtures thereof. Accordingly, the chemical structures depicted herein encompass all possible tautomeric forms of the illustrated compounds.

Compounds disclosed herein also include isotopically labeled compounds where one or more atoms have an atomic mass different from the atomic mass conventionally found in nature. Examples of isotopes that may be incorporated into the compounds include, but are not limited to, $^2$H, $^3$H, $^{11}$C, $^{13}$C, $^{14}$C, $^{15}$N, $^{17}$O and $^{18}$O.

Compounds may exist in unsolvated forms as well as solvated forms, including hydrated forms and as N-oxides. In general, the hydrated, solvated and N-oxide forms are within the scope of the present invention. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

4.3 Synthesis of Propofol Prodrug Compounds

The compounds of Formulae (I)-(V) and (XII)-(XIV) may be obtained via the synthetic methods illustrated in Schemes 1-3. Starting materials useful for preparing these compounds and intermediates thereof are commercially available or can be prepared by well-known synthetic methods (Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995).

A compound of Formula (I) wherein A is [H$_2$NCHR$^5$C(O)]— and X is —CH$_2$— (i.e. a compound of Formula (VIII)) may be prepared as illustrated in Scheme 1. The protected carboxylic acid (VI) is activated via a coupling agent (e.g., a carbodiimide) and reacted with propofol to afford compound of Formula (VII). Protecting group removal and acylation with an appropriately protected amino acid affords, after further deprotection, a compound of Formula (VIII).

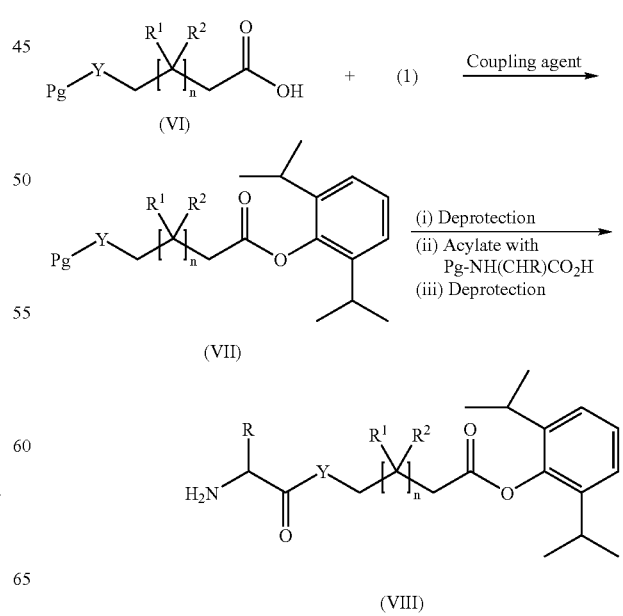

Propofol (1) is converted to the chloroformate derivative (2) by treatment with a phosgene equivalent as illustrated in Scheme 2.

Scheme 2

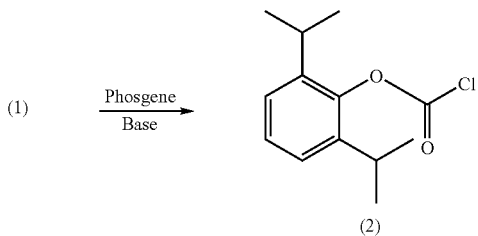

A compound of Formula (I) wherein A is [$H_2NCHR^5C(O)$]— and X is —O—, —$NR^4$— or —S— (i.e., a compound of Formula (XI)) may be prepared as illustrated in Scheme 3.

Scheme 3

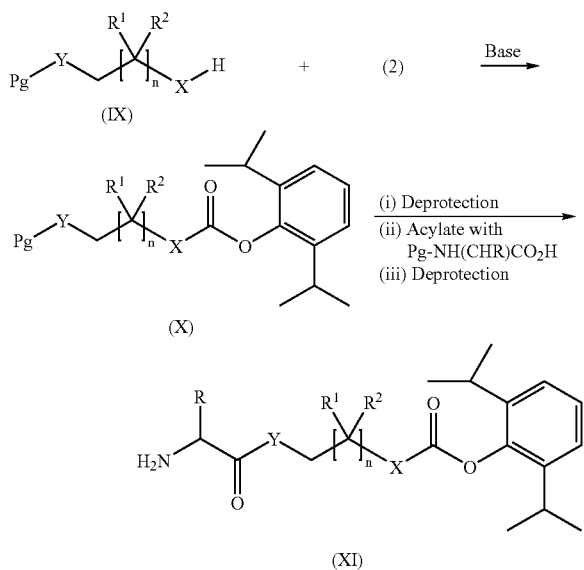

Other methods for synthesis of the compounds described herein and/or starting materials are either described in the art or will be readily apparent to the skilled artisan. Accordingly, the methods presented in Schemes 1-3 herein are illustrative rather than comprehensive.

4.4 Therapeutic/Prophylactic Uses and Methods of Administration

The compounds of Formulae (I)-(V) and (XII)-(XIV), as described herein, may be used to treat and/or prevent migraine in patients. The methods comprise administering to a patient a therapeutically effective amount of a compound of Formulae (I)-(V) and (XII)-(XIV) to treat and/or prevent migraine. In the therapeutic methods herein, a therapeutically effective amount of the compound is administered to a patient suffering from a migraine headache. In the prophylactic methods herein, a therapeutically effective amount of the compound is administered to a patient at risk of developing a migraine.

In some embodiments, the compounds are administered orally to treat and/or prevent migraine. However, in other embodiments, the compounds are administered parenterally (e.g., via inhalation or injection). In some embodiments, the compounds are administered in amounts of between about 10 mg to about 4 g to treat or prevent migraine.

The compounds of Formulae (I)-(V) and (XII)-(XIV) may also be used as anti-emetics and can be administered to patients at risk of vomiting and/or who are nauseous. For example, the compounds may be administered to patients that are being concurrently treated with various chemotherapy agents and/or surgical procedures, which induce nausea, in order to treat and/or prevent nausea and vomiting. Typically, a therapeutically effective amount of the compound is administered to a patient to treat and/or prevent nausea and vomiting.

In some embodiments, the compounds are administered orally to treat and/or prevent nausea or vomiting. However, in other embodiments, the compounds are administered parenterally (e.g., via inhalation or injection to treat and/or prevent nausea or vomiting. In some embodiments, the compounds are administered in amounts of between about 10 mg to about 4 g to treat and/or prevent nausea or vomiting.

The compounds of Formulae (I)-(V) and (XII)-(XIV) may also be used as hypnotic agents to induce and/or maintain general anesthesia and/or as a sedative. Typically, a therapeutically effective amount of the compound is administered to a patient to induce hypnosis, anesthesia and/or sedation.

In some embodiments, the compounds are administered intravenously when used as a general anesthetic. In other embodiments, the compounds are administered by inhalation. The compounds may be formulated by methods used to formulate propofol, which are well known in the art. In some embodiments, compounds of Formulae (I)-(V) and (XII)-(XIV) that are water soluble may be formulated as an injectable aqueous solution, which contains significantly less emulsifiers or solubilizers than used in aqueous formulations of propofol, thereby avoiding discomfort at the site of injection.

In some embodiments, the compounds are administered orally in amounts of about 10 mg to 4 g daily when used as a sedative (e.g., for the treatment of anxiety conditions). However, in other embodiments, the compounds may also be administered by inhalation, intravenously or intramuscularly when used as a sedative.

The compounds of Formulae (I)-(V) and (XII)-(XIV) may be administered in similar amounts and in the same schedule as described in the art for propofol. In one embodiment, dosage levels of the compounds of Formulae (I)-(V) and (XII)-(XIV) for producing general anesthesia, maintaining anesthesia and producing a sedative effect are as described in the art for propofol.

The compounds of Formulae (I)-(V) and (XII)-(XIV) may also be used to inhibit oxidation in biological materials. The methods involve contacting the biological material with an effective amount of the compound. In therapeutic methods herein, a therapeutically effective amount of the compound is administered to a patient suffering from a pathological condition treated by inhibition of oxidation. In prophylactic methods herein, a therapeutically effective amount of the compound is administered to a patient at risk of developing a disease as a result of exposure to oxidative stress. The compounds may find particular use in preventing and/or treating oxidation in disorders of the central nervous system that involve an inflammatory component.

The compounds of Formulae (I)-(V) and (XII)-(XIV) may be used to treat and/or prevent neurodegenerative conditions of the nervous system, which include, but are not limited to, Friedrich's disease, Parkinson's disease, Alzheimer's disease, Huntington's disease, amyotrophic lateral sclerosis (ALS), multiple sclerosis (MS) and Pick disease. In some embodiments, a therapeutically effective amount of a compound (e.g., between about 10 mg to about 4 g daily) is orally administered to treat and/or prevent chronic neurodegenerative diseases.

The compounds of Formulae (I)-(V) and (XII)-(XIV) may also be used to treat and/or prevent trauma to the central nervous system such as, for example, skull fracture and its resulting edema, concussion, contusion, brain hemorrhages, shearing lesions, subdural and epidural hematoma, and spinal cord injury (e.g., mechanical injury due to compression or flexion of the spinal cord). In some embodiments, a compound is parenterally administered by intravenous injection or injection directly into the central nervous system (i.e., intrathecally ("IT") or into the brain) to treat and/or prevent traumatic conditions of the central nervous system. In other embodiments, a therapeutically effective amount of a compound (e.g., between about 25 mg to about 500 mg IV or IM and between about 5 mg to about 100 mg IT) is administered to treat and/or prevent traumatic conditions of the central nervous system.

The compounds of Formulae (I)-(V) and (XII)-(XIV) may also be used as anti-convulsives to treat and/or prevent seizures (e.g., epileptic seizures). Methods for treating and/or preventing convulsions comprise administering a therapeutically effective amount of a compound to a patient in need of such treatment. In some embodiments, the compounds are administered orally to treat and/or prevent convulsions. In other embodiments, the compounds are parenterally administered to treat and/or prevent convulsions. In still other embodiments, the compounds are administered in amounts of between about 10 mg to about 4 g daily to treat and/or prevent convulsions.

When used to treat and/or prevent the above disease or disorders compounds and/or pharmaceutical compositions of Formulae (I)-(V) and (XII)-(XIV) may be administered or applied singly, or in combination with other agents. The compounds and/or compositions may also be administered or applied singly, or in combination with other pharmaceutically active agents, including other compounds of Formulae (I)-(V) and (XII)-(XIV).

Provided herein are methods of treatment and prophylaxis by administering to a patient a therapeutically effective amount of a composition or compound of Formulae (I)-(V) and (XII)-(XIV). The patient may be an animal, is more preferably, a mammal and even more preferably, a human.

The compounds of Formulae (I)-(V) and (XII)-(XIV) and/or pharmaceutical compositions thereof are preferably administered orally. The compounds and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin.

In specific embodiments, it may be desirable to administer one or more compounds and/or pharmaceutical compositions thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes or fibers. In one embodiment, administration can be by direct injection at the site (or former site) of cancer or arthritis.

In certain embodiments, it may be desirable to introduce one or more compounds and/or pharmaceutical compositions thereof into the central nervous system by any suitable route, including intraventricular, intrathecal and epidural injection. Intraventricular injection may be facilitated by use of an intraventricular catheter, for example, attached to a reservoir, such as an Ommaya reservoir.

In some embodiments, the compounds and/or pharmaceutical compositions can be delivered via sustained release systems, preferably oral sustained release systems. In one embodiment, a pump may be used (Langer, supra; Sefton, *CRC Crit Ref Biomed Eng.* 1987, 14, 201; Saudek et al., *N. Engl. J. Med.* 1989, 321, 574).

In other embodiments, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; Levy et al., *Science* 1985, 228, 190; During et al., *Ann. Neurol.* 1989, 25, 351; Howard et al., *J. Neurosurg.* 1989, 71,105).

In still other embodiments, polymeric materials are used for oral sustained release delivery. Polymers include, but are not limited to sodium carboxymethylcellulose, hydroxypropylcellulose, hydroxypropylmethylcellulose and hydroxyethylcellulose. Other cellulose ethers have been described (Alderman, *Int. J. Pharm. Tech. & Prod. Mfr.* 1984, 5(3), 1-9). Factors affecting drug release are well known to the skilled artisan and have been described in the art (Bamba et al., *Int. J. Pharm.* 1979, 2, 307).

In still other embodiments, enteric-coated preparations can be used for oral sustained release administration. Coating materials include, but are not limited to polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.* 2000, 26, 695-708). In still other embodiments, OROS™ osmotic devices are used for oral sustained release delivery devices (Theeuwes et al., U.S. Pat. No. 3,845,770; Theeuwes et al., U.S. Pat. No. 3,916,899).

For administration by inhalation, compounds may be conveniently delivered to the lung by a number of different devices. For example, a Metered Dose Inhaler ("MDI"), which utilizes canisters that contain a suitable low boiling propellant, e.g., dichlorodifluoromethane, trichlorofluoromethane, dichlorotetrafluoroethane, carbon dioxide or other suitable gas may be used to deliver compounds directly to the lung.

Alternatively, a Dry Powder Inhaler ("DPI") device may be used to administer a compound to the lung (See, e.g., Raleigh et al., *Proc. Amer. Assoc. Cancer Research Annual Meeting* 1999, 40, 397). DPI devices typically use a mechanism such as a burst of gas to create a cloud of dry powder inside a container, which may then be inhaled by the patient and are well known in the art and may be purchased from a number of commercial sources. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound and a suitable powder base such as lactose or starch for these systems.

Another type of device that may be used to deliver a compound to the lung is a liquid spray device supplied, for example, by Aradigm Corporation, Hayward, Calif. Liquid spray systems use extremely small nozzle holes to aerosolize liquid drug formulations that may then be directly inhaled into the lung.

In some embodiments, a nebulizer device is used to deliver a compound to the lung. Nebulizers create aerosols from liquid drug formulations by using, for example, ultrasonic energy to form fine particles that may be readily inhaled (e.g., Verschoyle et al., *British J. Cancer* 1999, 80, Suppl. 2, 96; Armer et al., U.S. Pat. No. 5,954,047; van der Linden et al., U.S. Pat. No. 5,950,619; van der Linden et al., U.S. Pat. No. 5,970,974).

In other embodiments, an electrohydrodynamic ("EHD") aerosol device is used to deliver a compound to the lung. EHD aerosol devices use electrical energy to aerosolize liquid drug solutions or suspensions (see e.g., Noakes et al., U.S. Pat. No. 4,765,539; Coffee, U.S. Pat. No. 4,962,885; Coffee, International Publication No., WO 94/12285; Coffee, International Publication No., WO 94/14543; Coffee, International Publication No., WO 95/26234, Coffee, International Publication No., WO 95/26235, Coffee, International Publication No., WO 95/32807). The electrochemical properties of a compound may be important parameters to optimize when delivering the compound to the lung with an EHD aerosol device, and such optimization is routinely performed by one of skill in the art. EHD aerosol devices may more efficiently deliver drugs to the lung than existing pulmonary delivery technologies. Other methods of intra-pulmonary delivery of a compound will be known to the skilled artisan.

The compounds of Formulae (I)-(V) and (XII)-(XIV) and/or compositions containing such compounds preferably provide therapeutic or prophylactic levels of propofol upon in vivo administration to a patient. While not wishing to bound by theory, the promoiety or promoieties of the compounds may be cleaved either chemically and/or enzymatically. One or more enzymes present in the stomach, intestinal lumen, intestinal tissue, blood, liver, brain or any other suitable tissue of a mammal may enzymatically cleave the promoiety or promoieties of the administered compounds.

While not wishing to bound by theory, the promoiety or promoieties of the compounds may be cleaved prior to absorption by the gastrointestinal tract (e.g., within the stomach or intestinal lumen) and/or after absorption by the gastrointestinal tract (e.g., in intestinal tissue, blood, liver or other suitable tissue of a mammal). Preferably, propofol remains conjugated to a promoiety during transit across the intestinal mucosal barrier to provide protection from presys-temic metabolism. In some embodiments, the compounds are essentially not metabolized to propofol within enterocytes, but are metabolized to the parent drug within the systemic circulation. Cleavage of the promoiety or promoieties of the compounds after absorption by the gastrointestinal tract may allow these prodrugs to be absorbed into the systemic circulation by passive diffusion. In one embodiment, the compounds are passively absorbed.

Cleavage of the promoiety or promoieties of the compounds of Formulae (I)-(V) and (XII)-(XIV) after absorption by the gastrointestinal tract, may allow these prodrugs to be absorbed into the systemic circulation from the large intestine. In some embodiments, the compounds and/or pharmaceutical compositions containing compounds of Formulae (I)-(V) and (XII)-(XIV) are preferably administered as sustained release systems. In other embodiments, the compounds and/or pharmaceutical compositions are delivered by oral sustained release administration. In these embodiments, the compounds and/or pharmaceutical compositions may be administered twice per day or once per day.

4.5 Pharmaceutical Compositions

The present pharmaceutical compositions contain a therapeutically effective amount of one or more compounds of Formulae (I)-(V) and (XII)-(XIV), preferably, in purified form, together with a suitable amount of a pharmaceutically acceptable vehicle, so as to provide the form for proper administration to a patient. When administered intravenously to a patient, the compounds and pharmaceutically acceptable vehicles are preferably sterile. Water is a preferred vehicle when a compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of Formulae (I)-(V) and (XII)-(XIV) may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds into preparations that can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington's Pharmaceutical Sciences, Philadelphia College of Pharmacy and Science, 19th Edition, 1995). Preferred pharmaceutical compositions are formulated for oral delivery.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optional agents, for example, sweetening agents such as fructose, aspartame or saccharin, flavoring agents such as peppermint, oil of wintergreen, or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds and pharmaceutical compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral pharmaceutical compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5 mM to about 50 mM), etc. Additionally, flavoring agents, preservatives, coloring agents, bile salts, acylcarnitines and the like may be added.

A compound of Formulae (I)-(V) and (XII)-(XIV) may also be formulated in rectal or vaginal pharmaceutical compositions such as suppositories or retention enemas, e.g., containing conventional suppository bases such as cocoa butter or other glycerides.

In addition to the formulations described previously, a compound of Formulae (I)-(V) and (XII)-(XIV) may also be formulated as a depot preparation. Such long acting formulations may be administered by implantation (for example subcutaneously or intramuscularly) or by intramuscular injection. Thus, for example, a compound may be formulated with suitable polymeric or hydrophobic materials (for example as an emulsion in an acceptable oil) or ion exchange resins, or as sparingly soluble derivatives, for example, as a sparingly soluble salt.

When a compound of Formulae (I)-(V) and (XII)-(XIV) is acidic, it may be included in any of the above-described formulations as the free acid, a pharmaceutically acceptable salt, a solvate, hydrate or N-oxide. Pharmaceutically acceptable salts substantially retain the activity of the free acid, may be prepared by reaction with bases and tend to be more soluble in aqueous and other protic solvents than the corresponding free acid form.

Liquid drug formulations suitable for use with nebulizers and liquid spray devices and EHD aerosol devices will typically include a compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the compounds. Preferably, this material is liquid such as an alcohol, glycol, polyglycol or a fatty acid. Other methods of formulating liquid drug solutions or suspension suitable for use in aerosol devices are known to those of skill in the art (e.g., Biesalski, U.S. Pat. No. 5,112,598; Biesalski, U.S. Pat. No. 5,556,611).

4.6 Combination Therapy

In certain embodiments, the compounds of Formulae (I)-(V) and (XII)-(XIV) can be used in combination therapy with at least one other therapeutic agent. The compound and the other therapeutic agent(s) can act additively or, more preferably, synergistically. In some embodiments, a composition comprising a propofol prodrug compound is administered concurrently with the administration of another therapeutic agent, such as for example, another sedative, hypnotic agent or anesthetic agent (e.g., propofol), which can be part of the same composition as the propofol prodrug compound or a different composition. For example, in the treatment of post-chemotherapy or post-operative nausea and vomiting compounds of Formulae (I)-(V) and (XII)-(XIV) may be administered together with 5-HT$_3$ antagonists (e.g., ondansetron, granisetron, dolasetron, palonosetron), corticosteroids (e.g., dexamethasone), dopamine antagonists (e.g., metoclopramide, droperidol, chlorpromazine) or other antiemetic agents (e.g., benzodiazepines such as diazepam or lorazepam; NK-1 antagonists such as aprepitant). In other embodiments, a composition comprising a propofol prodrug compound is administered prior or subsequent to administration of another therapeutic agent, such as, for example, another sedative, hypnotic agent or anesthetic agent, (e.g., propofol).

5. EXAMPLES

The invention is further defined by reference to the following examples, which describe preparation of compounds of Formulae (I)-(V) and (XII)-(XIV), compositions containing such compounds and assays for using such compounds and compositions. It will be apparent to those skilled in the art that many modifications, both to materials and methods, may be practiced without departing from the scope of the invention.

In the examples below, the following abbreviations have the following meanings. If an abbreviation is not defined, it has its generally accepted meaning.

Atm=atmosphere
Boc=tert-butyloxycarbonyl
Bzl=benzyl
Cbz=carbobenzyloxy
Dap=L-2,3-diaminopropionic acid
DCC=dicyclohexylcarbodiimide
DMAP=4-N,N-dimethylaminopyridine
DMEM=Dulbecco's minimum eagle medium
DMF=N,N-dimethylformamide
DMSO=dimethylsulfoxide
Fmoc=9-fluorenylmethyloxycarbonyl
g gram
h=hour
HBSS=Hank's buffered saline solution
L=liter
LC/MS=liquid chromatography/mass spectroscopy
M=molar
min=minute
mL=milliliter
mmol=millimoles
NHS=N-hydroxysuccinimide PBS=phosphate buffered saline
THF=tetrahydrofuran
TFA=trifluoroacetic acid
TMS=trimethylsilyl
μL=microliter
μM=micromolar
v/v=volume to volume

Example 1

2,6-(Diisopropyl)phenyl 1-[((2S)-2-amino-3-methyl-butyryl)aminomethyl]-1-Cyclohexane Acetate Hydrogen Formate Salt (3)

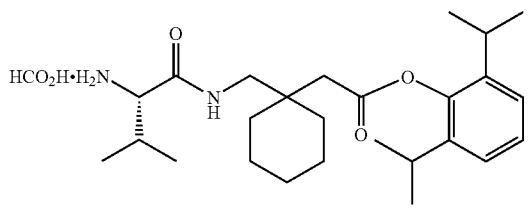

Step 1: 2,6-(Diisopropyl)phenyl 1-[(tert-butoxycarbonylaminomethyl]-1-Cyclohexane Acetate (4)

To a solution of N-Boc-gabapentin (4.0 g, 14.7 mmol) and propofol (2.67 g, 15 mmol) in toluene (40 mL) was added 1,3-dicyclohexylcarbodiimide (3.1 g, 15 mmol) followed by 4-(dimethylamino)pyridine (0.3 g, 2.4 mmol). The resulting mixture was heated to 90° C. and stirred for 14 h. The reaction mixture was then cooled to room temperature, filtered and the filtrate concentrated in vacuo. This crude residue was purified by flash chromatography on silica gel (eluting with a gradient of 100% hexane to 20% ethyl acetate in hexane) to provide title compound (4) (6.1 g, 96% yield). $^1$H-NMR (400 MHz, CDCl$_3$): δ 7.24-7.13 (m, 3H), 5.12 (br s, 1H), 3.28 (d, J=6.8 Hz, 2H), 2.92-2.86 (m, 2H), 2.64 (s, 2H), 1.62-1.43 (m, 19H), 1.18 (d, J=6.8 Hz, 12H).

Step 2: 2,6-(Diisopropyl)phenyl 1-Aminomethyl-1-Cyclohexane Acetate (5)

To a solution of compound (4) (6.1 g, 14.1 mmol) in dichloromethane (30 mL) was added trifluoroacetic acid (10 mL). The resulting mixture was stirred at room temperature for 3 h then the solvent was removed in vacuo. The crude product (5) was carried to next step without further purification.

Step 3: 2,6-(Diisopropyl)phenyl 1-[((2S)-2-amino-3-methylbutyryl)aminomethyl]-1-Cyclohexane Acetate Hydrogen Formate Salt (3)

To a solution of Boc-L-valine (730 mg, 3.36 mmol) in DMF (8 mL) was added diisopropylethylamine (1.3 mL, 7.46 mmol) followed by O-(benzotriazol-1-yl)-N,N,N',N'-tetramethyluronium hexafluorophosphate (1.3 g, 3.42 mmol). The resulting mixture was stirred at room temperature for 30 minutes after which was added a solution of compound (5) (1.5 g, 3.37 mmol) in DMF (2 mL) dropwise. The reaction was allowed to proceed at room temperature for 12 h. The reaction mixture was then diluted with ethyl acetate (50 mL) and the organic solution was washed with 10% aqueous citric acid solution (2×30 mL), saturated aqueous sodium bicarbonate solution (2×30 mL) and brine (2×30 mL). The organic layer was dried over magnesium sulfate, filtered and then concentrated in vacuo. The crude residue was then dissolved in dichloromethane (10 mL) and treated with trifluoroacetic acid (3 mL). The reaction mixture was stirred at room temperature for 3 h then the solvent removed in vacuo. The crude product was purified by reverse phase LC/MS to afford the title compound (3) as a hydrogen formate salt (0.66 g, 46% yield). $^1$H-NMR (400 MHz, CD$_3$OD): δ 8.50 (s, 1H), 7.21-7.14 (m, 3H), 3.63-3.35 (ABq, J=96, 13.6 Hz, 2H), 3.56 (d, J=5.6 Hz, 1H), 2.98-2.92 (m, 2H), 2.74 (s, 2H), 2.16-2.11 (m, 1H), 1.65-1.48 (m, 10H), 1.17 (d, J=6.8 Hz, 12H), 1.05 (d, J=7.2 Hz, 3H), 1.02 (d, J=6.8 Hz, 3H). MS (ESI) m/z 431.47 (M+H)$^+$.

Example 2

2,6-(Diisopropyl)phenyl 1-[((2S)-2-amino-3-hydroxypropionyl)aminomethyl]-1-Cyclohexane Acetate Trifluoroacetate Salt (6)

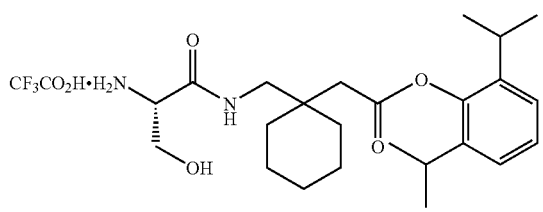

Following procedures for the preparation of compound (3) and substituting Boc-L-valine with Boc-L-serine provided the title compound (6) as its trifluoroacetate salt. $^1$H-NMR (400 MHz, CD$_3$OD): δ 7.18-7.14 (m, 3H), 3.92-3.87 (m, 2H), 3.80 (m, 1H), 3.58-3.40 (Abq, J=60.4, 13.6 Hz, 2H), 2.98-2.92 (m, 2H), 2.74 (s, 2H), 2.16-2.11 (m, 1H), 1.64-1.48 (m, 10H), 1.17 (d, J=6.8 Hz, 12H). MS (ESI) m/z 419.41 (M+H)$^+$.

Example 3

2,6-(Diisopropyl)phenyl 1-[((2S)-2-amino-(3R)-3-hydroxybutyryl)aminomethyl]-1-Cyclohexane Acetate Trifluoroacetate Salt (7)

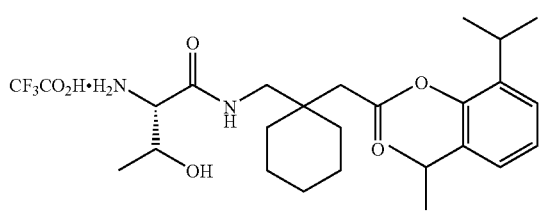

Following procedures for the preparation of compound (3) and substituting Boc-L-valine with Boc-L-threonine provided the title compound (7) as its trifluoroacetate salt. $^1$H-NMR (400 MHz, CD$_3$OD): δ 7.19-7.14 (m, 3H), 4.03 (m, 1H), 3.63 (d, J=6.0 Hz, 1H), 3.61-3.39 (ABq, J=74.8, 13.6 Hz, 2H), 2.98-2.91 (m, 2H), 2.74 (s, 2H), 1.65-1.48 (m, 10H), 1.28 (d, J=6.4 Hz, 3H), 1.17 (d, J=6.8 Hz, 12H). MS (ESI) m/z 433.43 (M+H)$^+$.

Example 4

2,6-(Diisopropyl)phenyl 4-[(2S)-2-amino-3-carbamoylpropionylamino]-3,3-dimethylbutanoate Hydrogen Formate Salt (8)

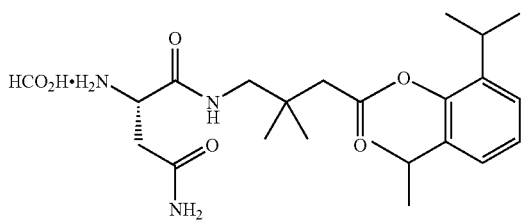

Step 1: 4-[2,6-(Diisopropyl)phenoxycarbonyl]-3,3-dimethylbutanoic Acid (9)

To a mixture of 3,3-dimethylglutaric anhydride (3.87 g, 27.2 mmol) and propofol (27.2 mmol) was added triethylamine followed by catalytic amount of 4-dimethylaminopyridine. The resulting mixture was heated in a sealed vessel at 100° C. for 14 h. The mixture was then cooled to room temperature and diluted with ethyl acetate (100 mL). The organic layer was washed with 10% aqueous citric acid solution (2×30 mL), brine (2×30 mL) and dried over $MgSO_4$. The solvent was then removed in vacuo and the crude residue was purified by flash chromatography on silica gel (eluting with a gradient of 100% hexane to 40% hexane in ethyl acetate) to afford the title compound (9) as a colorless oil (5.7 g, 65% yield). $^1$H-NMR (400 MHz, $CDCl_3$): δ 7.16-7.11 (m, 3H), 2.93-2.89 (m, 2H), 2.82 (s, 2H), 2.63 (s, 2H), 1.25 (s, 6H), 1.18 (d, J=6.8 Hz, 12H).

Step 2: 2,6-(Diisopropyl)phenyl 3,3-dimethyl-4-(benzyloxycarbonylamino)butanoate (10)

To a cooled (0° C.) solution of compound (9) (5.66 g, 17.6 mmol) in anhydrous acetone was added triethylamine (2.34 mL, 16.8 mmol) followed by ethyl chloroformate (1.6 mL, 16.7 mmol) dropwise. The resulting mixture was stirred for 10 min, and then a solution of sodium azide (1.7 g, 26.1 mmol) in water (20 mL) was added. The resulting reaction mixture was stirred for additional 30 min before it was poured onto ice water (100 mL). The aqueous solution was extracted with toluene (2×100 mL). The layers were separated and the combined organic layers were dried over MgSO4. The solvent was reduced to 50 mL in vacuo. To this solution, benzyl alcohol (2.7 mL, 26.1 mmol) was added and the reaction mixture heated under reflux for 14 h. The mixture was then cooled to room temperature and the solvent removed in vacuo. The residue was purified by flash chromatography on silica gel (eluting with a gradient of 100% hexane to 20% ethyl acetate in hexane) to afford the title compound (10) as a colorless oil (5.51 g, 73% yield). $^1$H-NMR (400 MHz, $CDCl_3$): δ 7.36-7.12 (m, 8H), 5.10 (s, 2H), 3.24 (d, J=6.8 Hz, 2H), 2.92-2.87 (m, 2H), 2.57 (s, 2H), 1.25 (s, 6H), 1.18 (d, J=6.8 Hz, 12H), 1.14 (s, 6H).

Step 3: 2,6-(Diisopropyl)phenyl 4-amino-3,3-dimethylbutanoate hydrochloride (11)

To a sample of compound (10) was added 10% palladium on carbon (500 mg). After degassing with $N_2$, the reaction mixture was dissolved in ethyl acetate (100 mL), followed by addition of 4 N HCl in dioxane (20 mL). The resulting solution was degassed once more and a hydrogen balloon was added atop. The suspended solution was stirred at room temperature for 4 h, and then was filtered through Celite and concentrated in vacuo. The crude product (11) was carried to next step without further purification. $^1$H-NMR (400 MHz, $CD_3OD$): δ 7.18-7.11 (m, 3H), 3.03 (s, 2H), 2.96-2.89 (m, 2H), 2.74 (s, 2H), 1.24 (s, 6H), 1.18-1.14 (d, J=7.2 Hz, 12H). MS (ESI) m/z 292.2 $(M+H)^+$.

Step 4: 2,6-(Diisopropyl)phenyl 4-[(2S)-2-amino-3-carbamoylpropionylamino]-3,3-dimethylbutanoate Hydrogen Formate Salt (8)

To a solution of Boc-L-Asn (200 mg, 0.86 mmol) in DMF (2 mL) was added diisopropylethylamine (0.35 mL, 2.0 mmol) followed by O-(benzotriazol-1-yl)-N,N,N',N'-tetramethyluronium hexafluoro-phosphate (0.35 g, 0.92 mmol). The resulting mixture was stirred at room temperature for 15 minutes after which was added a solution of compound (11) (0.28 g, 0.85 mmol) in DMF (2 mL) dropwise. The reaction was allowed to proceed at room temperature for 12 h. The reaction mixture was then diluted with ethyl acetate (30 mL) and washed with 10% aqueous citric acid solution (2×20 mL), saturated aqueous sodium bicarbonate solution (2×20 mL) and brine (2×20 mL). The organic layer was dried over magnesium sulfate, filtered and then concentrated in vacuo. The crude product was then dissolved in dichloromethane (4 mL) and treated with trifluoroacetic acid (2 mL). The reaction mixture was stirred at room temperature for 3 h then the solvent removed in vacuo. The crude product was purified by reverse phase LC/MS to afford the title compound (8) as a hydrogen formate salt (51 mg, 15% yield). $^1$H-NMR (400 MHz, $CD_3OD$): δ 8.48 (s, 1H), 7.21-7.14 (m, 3H), 3.40-3.24 (ABq, J=61.6, 13.6 Hz, 2H), 3.01 (s, 2H), 2.94-2.88 (m, 2H), 2.81 (s, 2H), 1.23-1.13 (m, 10H), 1.17 (m, 18H). MS (ESI) m/z 406.3 $(M+H)^+$.

Example 5

2,6-(Diisopropyl)phenyl 4-[(2S)-2-amino-3-carboxypropionylamino]-3,3-dimethylbutanoate Trifluoroacetate Salt (12)

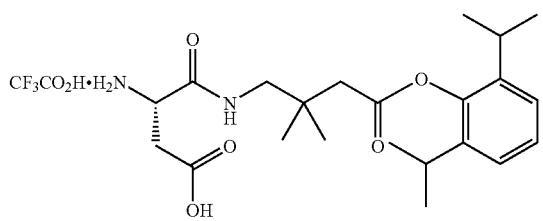

Following procedures for the preparation of compound (8) and substituting Boc-L-Asn with Boc-L-Asp(O$^t$Bu) provided the title compound (12). $^1$H-NMR (400 MHz, $CD_3OD$): δ 7.18-7.13 (m, 3H), 4.11 (dd, J=8.8, 5.2 Hz, 1H), 3.40-3.22 (ABq, J=58.0, 13.6 Hz, 2H), 2.96-2.89 (m, 2H), 2.76-2.58 (m, 4H), 1.18 (d, J=7.2 Hz, 12H), 1.14 (s, 6H). MS (ESI) m/z 407.3 $(M+H)^+$.

Example 6

2,6-(Diisopropyl)phenyl 4-[(2S)-2,3-diaminopropionylamino]-3,3-dimethylbutanoate Bis Trifluoroacetate Salt (13)

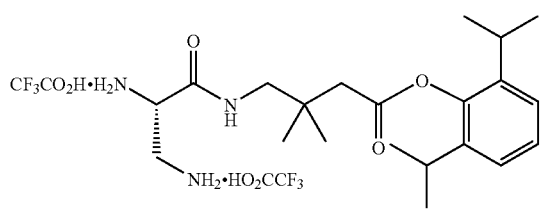

Following procedures for the preparation of compound (8) and substituting Boc-L-Asn with Boc-L-Dap(Boc) provided the title compound (13). $^1$H-NMR (400 MHz, CD$_3$OD): δ 7.20-7.13 (m, 3H), 3.78 (s, 1H), 3.37-3.26 (ABq, J=29.2, 13.2 Hz, 2H), 3.08-3.06 (m, 1H), 2.96-2.90 (m, 2H), 2.65 (s, 2H), 1.18 (d, J=6.4 Hz, 12H), 1.15 (s, 6H). MS (ESI) m/z 378.3 (M+H)$^+$.

Example 7

2,6-(Diisopropyl)phenyl 4-[(2S)-2-amino-3-hydroxypropionylamino]-3,3-dimethylbutanoate Trifluoroacetate Salt (14)

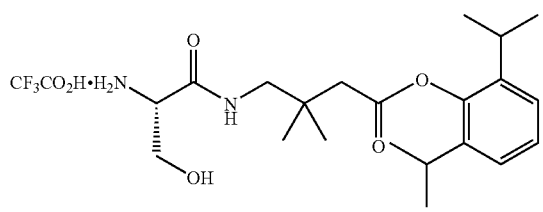

Following procedures for the preparation of compound (8) and substituting Boc-L-Asn with Boc-L-Ser provided the title compound (14). $^1$H-NMR (400 MHz, CD$_3$OD): δ 7.20-7.13 (m, 3H), 3.92-3.89 (m, 2H), 3.84-3.81 (m, 1H), 3.41-3.23 (ABq, J=58.0, 13.6 Hz, 2H), 2.94-2.89 (m, 2H), 2.64 (s, 2H), 1.18 (d, J=6.8 Hz, 12H), 1.15 (s, 6H). MS (ESI) m/z 379.3 (M+H)$^+$.

Example 8

2,6-(Diisopropyl)phenyl 4-[(2S)-2-aminopropionylamino]-3,3-dimethylbutanoate Trifluoroacetate Salt (15)

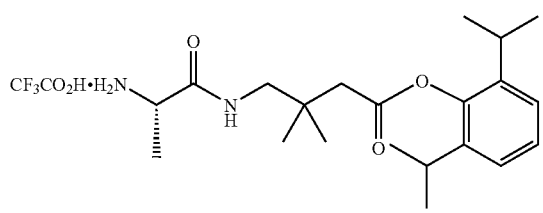

Following procedures for the preparation of compound (8) and substituting Boc-L-Asn with Boc-L-Ala provided the title compound (15). $^1$H-NMR (400 MHz, CD$_3$OD): δ 7.20-7.13 (m, 3H), 3.94 (q, J=6.8 Hz, 1H), 3.39-3.23 (ABq, J=51.6, 13.6 Hz, 2H), 2.96-2.89 (m, 2H), 2.63 (s, 2H), 1.53 (d, J=7.2 Hz, 3H), 1.18 (d, J=7.2 Hz, 12H), 1.15 (d, J=2.0 Hz, 6H). MS (ESI) m/z 363.3 (M+H)$^+$.

Example 9

2,6-(Diisopropyl)phenyl 4-[(2S)-2-amino-(3R)-3-hydroxybutyryl]amino-3,3-dimethylbutanoate Trifluoroacetate Salt (16)

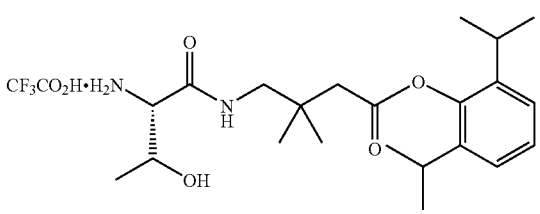

Following procedures for the preparation of compound (8) and substituting Boc-L-Asn with Boc-L-Thr(O$^t$Bu) provided the title compound (16). $^1$H-NMR (400 MHz, CD$_3$OD): δ 7.18-7.13 (m, 3H), 4.06-4.03 (m, 1H), 3.65 (d, J=6.0 Hz, 1H), 3.43-3.23 (ABq, J=67.2, 13.6 Hz, 2H), 2.96-2.89 (m, 2H), 2.64 (s, 2H), 1.32 (d, J=6.4 Hz, 3H), 1.18 (d, J=6.8 Hz, 12H), 1.15 (s, 6H). MS (ESI) m/z 393.3 (M+H)$^+$.

Example 10

2,6-(Diisopropyl)phenyl 4-[(2S)-2-amino-(4-hydroxyphenyl)propionylamino]-3,3-dimethylbutanoate Trifluoroacetate Salt (17)

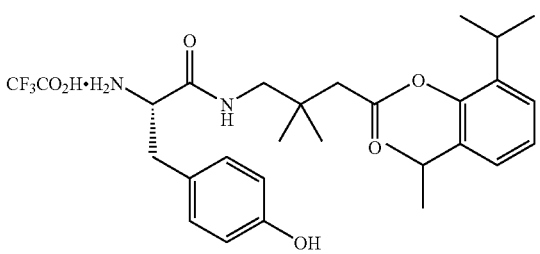

Following procedures for the preparation of compound (8) and substituting Boc-L-Asn with Boc-L-Tyr provided the title compound (17). $^1$H-NMR (400 MHz, CD$_3$OD): δ 7.18-7.13 (m, 3H), 7.07 (d, J=8.8 Hz, 2H), 6.74 (d, J=8.8 Hz, 2H), 3.89 (t, J=7.2 Hz, 1H), 3.34-3.12 (ABq, J=76.0, 13.6 Hz, 2H), 3.06-3.01 (dd, J=13.6, 6.8 Hz, 1H), 2.96-2.88 (m, 3H), 2.56-2.47 (ABq, J=19.6, 15.2 Hz, 2H), 1.18 (d, J=6.4 Hz, 12H), 1.15 (d, J=6.0 Hz, 6H). MS (ESI) m/z 455.3 (M+H)$^+$.

Example 11

2,6-(Diisopropyl)phenyl 4-[(2S)-2-amino-(indol-3-yl)propionylamino]-3,3-dimethylbutanoate Trifluoroacetate Salt (18)

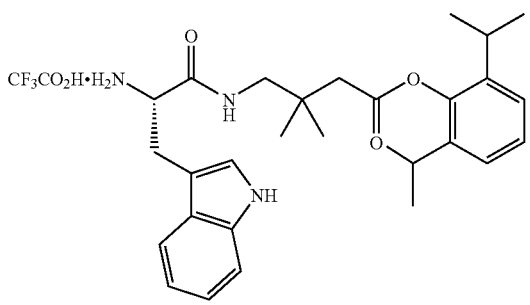

Following procedures for the preparation of compound (8) and substituting Boc-L-Asn with Boc-L-Trp provided the title compound (18). $^1$H-NMR (400 MHz, CD$_3$OD): δ 7.63 (d, J=8.0 Hz, 1H), 7.35 (d, J=8.4 Hz, 1H), 7.17-7.02 (m, 6H), 4.12 (t, J=7.6 Hz, 1H), 3.39-3.33 (dd, J=14.4, 7.2 Hz, 1H), 3.28-3.14 (m, 3H), 2.94-2.86 (m, 2H), 2.50-2.41 (ABq, J=20.8, 15.2 Hz, 2H), 1.17 (d, J=6.8 Hz, 12H), 0.99 (d, J=3.3 Hz, 6H). MS (ESI) m/z 478.3 (M+H)$^+$.

Example 12

2,6-(Diisopropyl)phenyl 4-[aminomethylcarbonylamino]-3,3-dimethylbutanoate Trifluoroacetate Salt (19)

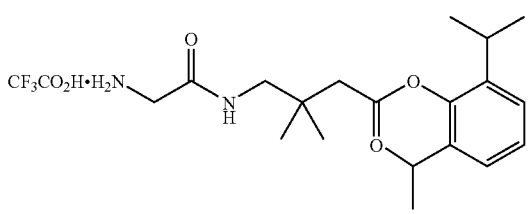

Following procedures for the preparation of compound (8) and substituting Boc-L-Asn with Boc-Gly provided the title compound (19). $^1$H-NMR (400 MHz, CD$_3$OD): δ 7.18-7.14 (m, 3H), 3.72 (s, 2H), 3.31 (s, 2H), 2.94-2.91 (m, 2H), 2.63 (s, 2H), 1.17 (d, J=6.8 Hz, 12H), 1.14 (s, 6H). MS (ESI) m/z 349.3 (M+H)$^+$.

Example 13

2,6-(Diisopropyl)phenyl 4-[(2S)-2-amino-4-carboxybutyrylamino]-3,3-dimethylbutanoate Trifluoroacetate Salt (20)

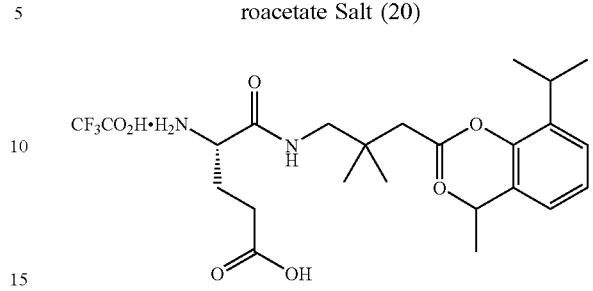

Following procedures for the preparation of compound (8) and substituting Boc-L-Asn with Boc-L-Glu(O$^t$Bu) provided the title compound (20). $^1$H-NMR (400 MHz, CD$_3$OD): δ 7.18-7.14 (m, 3H), 3.92 (t, J=7.2 Hz, 1H), 3.40-3.25 (ABq, J=42, 13.6 Hz, 2H), 2.96-2.89 (m, 2H), 2.64 (d, J=0.8 Hz, 2H), 2.46 (t, J=6.8 Hz, 2H), 2.13-2.08 (m, 2H), 1.17 (d, J=7.2 Hz, 12H), 1.15 (d, J=1.6 Hz, 6H). MS (ESI) m/z 421.3 (M+H)$^+$.

Example 14

2,6-(Diisopropyl)phenyl 4-[(2S)-2,6-diaminohexanoylamino]-3,3-dimethylbutanoate Bis Trifluoroacetate Salt (21)

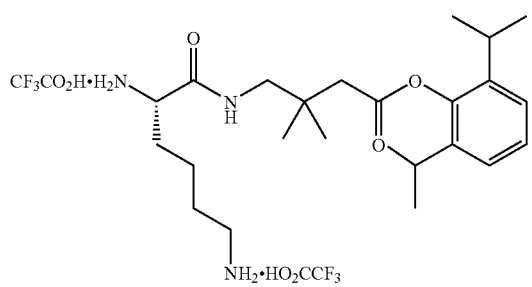

Following procedures for the preparation of compound (8) and substituting Boc-L-Asn with Boc-L-Lys(Boc) provided the title compound (21). $^1$H-NMR (400 MHz, CD$_3$OD): δ 7.21-7.14 (m, 3H), 3.88 (s, 1H), 3.32 (s, 2H), 2.96-2.89 (m, 4H), 2.64 (s, 2H), 1.91-1.85 (m, 2H), 1.70-1.68 (m, 2H), 1.49 (m, 2H), 1.18-1.14 (m, 18H). MS (ESI) m/z 420.4 (M+H)$^+$.

Example 15

2,6-(Diisopropyl)phenyl 4-[(2S)-pyrrolidin-2-ylcarbonylamino]-3,3-dimethylbutanoate Trifluoroacetate Salt (22)

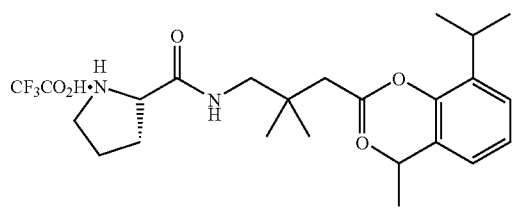

Following procedures for the preparation of compound (8) and substituting Boc-L-Asn with Boc-L-Pro provided the title compound (22). ¹H-NMR (400 MHz, CD₃OD): δ 7.21-7.14 (m, 3H), 4.29-4.25 (m, 1H), 3.41-3.25 (m, 4H), 2.96-2.89 (m, 2H), 2.64 (s, 2H), 2.48-2.42 (m, 1H), 2.08-1.99 (m, 3H), 1.18-1.14 (m, 18H). MS (ESI) m/z 389.37 (M+H)⁺.

Example 16

2,6-(Diisopropyl)phenyl 4-[(2S)-2-amino-3-methyl-butyrylamino]-3,3-dimethylbutanoate Trifluoroacetate Salt (23)

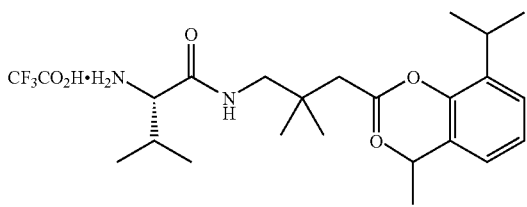

Following procedures for the preparation of compound (8) and substituting Boc-L-Asn with Boc-L-Val provided the title compound (23). ¹H-NMR (400 MHz, CD₃OD): δ 7.18-7.14 (m, 3H), 3.67 (d, J=5.2 Hz, 1H), 3.47-3.19 (ABq, J=98, 13.6 Hz, 2H), 2.96-2.89 (m, 2H), 2.64 (s, 2H), 2.22-2.17 (m, 1H), 1.18-1.14 (d, J=7.2 Hz, 12H), 1.14 (d, J=8.4 Hz, 6H), 1.09 (d, J=7.2 Hz, 3H), 1.06 (d, J=6.8 Hz, 3H). MS (ESI) m/z 391.4 (M+H)⁺.

Example 17

2-[2,6-(Diisopropyl)phenoxycarbonyloxy]ethyl (2S)-2-amino-3-carbamoylpropionate (24)<

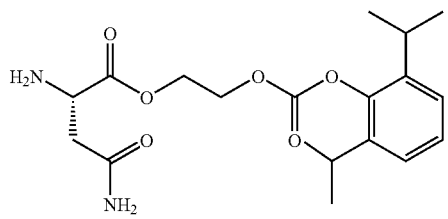

Step 1: (2,6-Diisopropyl)phenoxycarbonyl Chloride (2)

A 20% solution of phosgene in toluene (139 mL, 0.269 mol) was added to a stirring solution of propofol (40 g, 0.225 mmol) in toluene (80.0 mL) under a nitrogen atmosphere at 0° C. N,N-Dimethylaniline (34.0 mL, 0.269 mmol) was added dropwise over 15 minutes. The reaction mixture was allowed to warm to room temperature slowly and stirred for 14 h. The reaction mixture was filtered through Celite and the solvent was removed in vacuo. The crude product (2) was carried to the next step without further purification. ¹H-NMR (400 MHz, CDCl₃): δ 7.29-7.25 (m, 1H), 7.19-7.17 (m, 2H), 3.04-3.01 (m, 2H), 1.25 (d, J=7.2 Hz, 12H).

Step 2:
2-[2,6-(Diisopropyl)phenoxycarbonyloxy]ethanol (25)

To a cooled (0° C.) solution of ethylene glycol (1.0 g, 16.1 mmol) in dichloromethane was added pyridine (2.7 mL, 33.3 mmol) followed by chlorotrimethylsilane (2.24 mL, 17.7 mmol). The resulting solution was stirred at 0° C. for 30 minutes, and then compound (2) (6 mL, 2.15 M in dichloromethane) was added dropwise. The reaction mixture was allowed to warm to room temperature and stirred for 14 h. The mixture was then diluted with 10% aqueous citric acid solution (30 mL) and extracted with dichloromethane (2×20 mL). The combined organic layers were dried over MgSO₄, and the solvent was removed in vacuo. The crude product (25) was carried to the next step without further purification. ¹H-NMR (400 MHz, CDCl₃): δ 7.04-6.96 (m, 3H), 4.18-4.15 (dd, J=6.0, 4.8 Hz, 2H), 3.70 (d, J=4.8 Hz, 2H), 2.88-2.85 (m, 2H), 1.06 (d, J=6.8 Hz, 12H).

Step 3: 2-[2,6-(Diisopropyl)phenoxycarbonyloxy] ethyl (2S)-2-amino-3-carbamoylpropionate (24)

To a solution of Boc-L-Asn(trityl) (0.7 g, 1.47 mmol) and compound (25) (0.39 g, 1.46 mmol) in acetonitrile (4 mL) was added 1,3-dicyclohexylcarbodiimide (0.31 g, 1.5 mmol) followed by 4-dimethylaminopyridine (0.03 g, 0.24 mmol). The resulting mixture was stirred at room temperature for 14 h. The reaction mixture was then filtered and the filtrate was concentrated in vacuo. The crude residue was redissolved in dichloromethane (4 mL) and treated with trifluoroacetic acid (2 mL). The reaction mixture was stirred at room temperature for 4 h then concentrated in vacuo. The crude product was purified by reverse phase LC/MS purification to afford the title compound (24) as a white solid (21 mg, 3.8% yield). ¹H-NMR (400 MHz, CD₃OD): δ 7.23-7.12 (m, 3H), 4.51-4.47 (dd, J=9.2, 8.0 Hz, 4H), 4.12 (t, J=4.8 Hz, 1H), 3.02-2.97 (m, 2H), 2.85 (d, J=5.2 Hz, 2H), 1.19 (d, J=6.8 Hz, 12H). MS (ESI) m/z 381.3 (M+H)⁺.

Example 18

2-[2,6-(Diisopropyl)phenoxycarbonyloxy]ethyl (2S)-2-amino-3-hydroxypropionate (26)

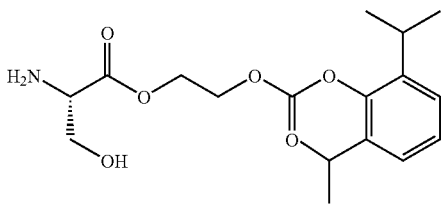

Following procedures for the preparation of compound (24) and substituting Boc-L-Asn(trityl) with Boc-L-Ser (O'Bu) provided the title compound (26). ¹H-NMR (400 MHz, CD₃OD): δ 7.22-7.15 (m, 3H), 4.54-4.51 (m, 4H), 4.13 (t, J=3.6 Hz, 1H), 4.03-3.96 (m, 2H), 3.02-2.97 (m, 2H), 1.19 (d, J=6.8 Hz, 12H). MS (ESI) m/z 354.3 (M+H)⁺.

Example 19

2-[2,6-(Diisopropyl)phenoxycarbonyloxy]ethyl (2S)-2-amino-3-carbamoylpropionamide Trifluoroacetate Salt (27)

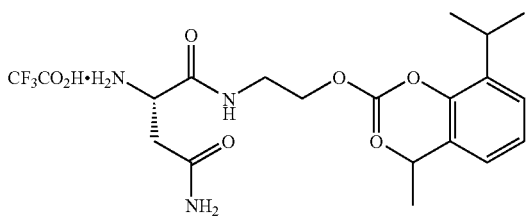

Step 1: 1-(Tert-butoxycarbonylamino)-2-[2,6-(diisopropyl)phenoxy-carbonyloxy]-ethane (28)

To an stirring, ice cold solution of Boc-Glycinol (600 mg, 3.72 mmol) and compound (2) (895 mg, 3.72 mmol) in dichloromethane (10 mL) was added triethylamine (658 µL, 3.91 mmol) dropwise followed by a catalytic amount of dimethylaminopyridine (45.0 mg, 0.372 mmol). The resulting mixture was allowed to warm to room temperature and stirred for 12 h. The mixture was then diluted with ethyl acetate (50 mL) and washed with 10% aqueous citric acid solution (2×30 mL), brine (2×30 mL), dried over MgSO$_4$, filtered and concentrated in vacuo. The crude oil was purified by flash chromatography on silica gel (eluting with a gradient of 100% hexane to 10% ethyl acetate in hexane) to provide title compound (27) (394 mg, 29% yield) as a clear oil. $^1$H-NMR (400 MHz, CD$_3$OD): δ 7.14-7.22 (m, 3H), 4.26 (t, J=5.6 Hz, 2H), 3.37 (t, J=5.2 Hz, 2H), 2.97-3.05 (m, 2H), 1.45 (s, 9H), 1.19 (d, J=7.2 Hz, 12H). MS (ESI) m/z 388.39 (M+Na)$^+$.

Step 2: 1-Amino-2-[2,6-(diisopropyl)phenoxycarbonyloxy]ethane Hydrochloride (29)

Compound (28) was dissolved in a solution of 4M HCl in dioxane and the reaction mixture was allowed to stir for 1 h. The solvent was removed in vacuo and some of the crude residue was purified by reverse phase LC/MS after which 1 equivalent of 1N HCl was added and the resulting liquid frozen and lyophilized to afford the title compound (29). $^1$H-NMR (400 MHz, CD$_3$OD): δ 7.17-7.23 (m, 3H), 4.26 (t, J=4.8 Hz, 2H), 3.35 (t, J=5.2 Hz, 2H), 2.98-3.06 (m, 2H), 1.19 (d, J=6.8 Hz, 12H). MS (ESI) m/z 266.20 (M+H)$^+$. The remaining material was carried on to the next step without further purification.

Step 3: 2-[2,6-(Diisopropyl)phenoxycarbonyloxy]ethyl (2S)-2-(tert-butoxycarbonylamino)-3-carbamoylpropionamide (30)

To a solution of Boc-L-asparagine (270 mg, 1.16 mmol) in DMF (2 mL) was added diisopropylethylamine (389 µL, 2.23 mmol) followed by O-(7-azabenzotriazol-1-yl)-N,N,N',N'-tetramethyluronium hexafluoro-phosphate (441 mg, 1.16 mmol). The resulting mixture was stirred at room temperature for 30 minutes after which was added dropwise a solution of (29) (237 mg, 0.893 mmol) in DMF and the reaction was allowed to proceed for 2 h. The reaction mixture was then diluted with ethyl acetate (40 mL and washed with 10% aqueous citric acid solution (2×30 mL), saturated aqueous sodium bicarbonate solution (2×30 mL) and brine (2×30 mL). The organic layer was dried over magnesium sulfate, filtered, and then concentrated in vacuo. The crude compound (30) was used without further purification.

Step 4: 2-[2,6-(Diisopropyl)phenoxycarbonyloxy]ethyl (2S)-2-amino-3-carbamoylpropionamide Trifluoroacetate Salt (27)

The crude compound (30) from above was dissolved in dichloromethane (6 mL) and treated with TFA (2 mL) at room temperature for 1 h. The solvent was removed in vacuo and the crude residue was purified by reverse phase LC/MS to afford the title compound (27) (144 mg, 43% yield over two steps). $^1$H-NMR (400 MHz, CD$_3$OD): δ 7.15-7.23 (m, 3H), 4.32 (t, J=5.6 Hz, 2H), 4.17 (dd, J=8.8, 4.4 Hz, 1H), 3.59 (t, J=5.2 Hz, 2H), 2.96-3.05 (m, 2H), 2.72-2.89 (m, 2H), 1.19 (dd, J=6.8, 1.2 Hz, 12H). MS (ESI) m/z 380.77 (M+H)$^+$.

Example 20

2-[2,6-(Diisopropyl)phenoxycarbonyloxy]ethyl Glycinamide Trifluoroacetate Salt (31)

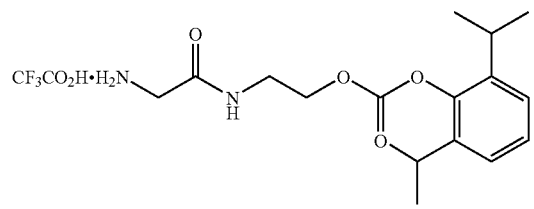

Following procedures for the preparation of compound (27) and substituting Boc-glycine for Boc-L-asparagine in Step 3 of Example 19 provided the title compound (31). $^1$H-NMR (400 MHz, CD$_3$OD): δ 7.15-7.23 (m, 3H), 4.32 (t, J=5.2 Hz, 2H), 3.68 (s, 2H), 3.60 (t, J=5.2 Hz, 2H), 2.95-3.03 (m, 2H), 1.19 (d, J=7.2 Hz, 12H). MS (ESI) m/z 323.74 (M+H)$^+$.

Example 21

2-[2,6-(Diisopropyl)phenoxycarbonyloxy]ethyl (2S)-2,6-diaminohexanoylamide Bis Trifluoroacetate Salt (32)

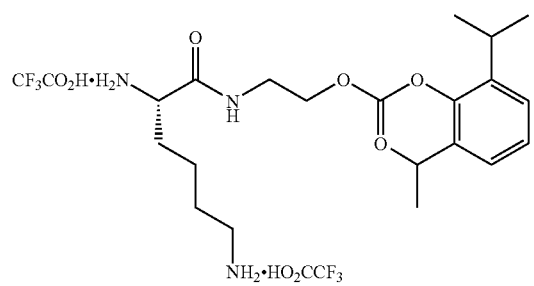

Following procedures for the preparation of compound (27) and substituting Boc-L-Lys(Boc) for Boc-L-asparagine in Step 3 of Example 19 provided the title compound (32). ¹H-NMR (400 MHz, CD₃OD): δ 7.16-7.24 (m, 3H), 4.28-4.41 (m, 2H), 3.82 (t, J=6 Hz, 1H), 3.54-3.68 (m, 2H), 2.95-3.03 (m, 2H), 2.92 (t, J=8 Hz, 2H), 1.83-1.93 (m, 2H), 1.67-1.72 (m, 2H), 1.48-1.53 (m, 2H), 1.20 (d, J=6.8 Hz, 12H). MS (ESI) m/z 394.85 (M+H)⁺.

Example 22

2-[2,6-(Diisopropyl)phenoxycarbonyloxy]ethyl (2S)-2-amino-3-hydroxypropionamide Trifluoroacetate Salt (33)

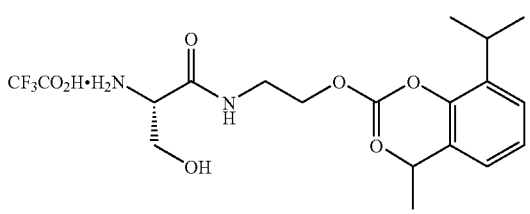

Following procedures for the preparation of compound (27) and substituting Boc-L-Ser(OᵗBu) for Boc-L-asparagine in Step 3 of Example 19 provided the title compound (33). ¹H-NMR (400 MHz, CD₃OD): δ 7.15-7.22 (m, 3H), 4.32 (t, J=4.6 Hz, 2H), 3.93 (t, J=3.6 Hz, 2H), 3.79-3.84 (dd, J=12, 8.8 Hz, 1H), 3.60 (t, J=5.2 Hz, 2H), 2.94-3.03 (m, 2H), 1.19 (d, J=7.2 Hz, 12H). MS (ESI) m/z 353.61 (M+H)⁺.

Example 23

2-[2,6-(Diisopropyl)phenoxycarbonyloxy]ethyl (2S)-2-amino-(4-hydroxyphenyl)propionamide Trifluoroacetate Salt (34)

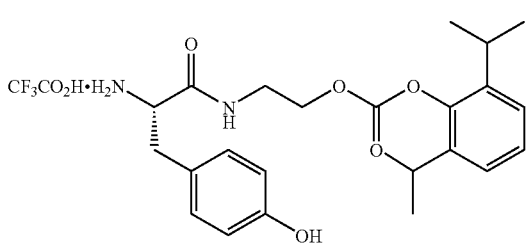

Following procedures for the preparation of compound (27) and substituting Boc-L-Tyr for Boc-L-asparagine in Step 3 of Example 19 provided the title compound (34). ¹H-NMR (400 MHz, CD₃OD): δ 7.14-7.22 (m, 3H), 7.09 (d, J=8.4 Hz, 2H), 6.77 (d, J=8.0 Hz, 2H), 4.27 (t, J=4.0 Hz, 2H), 3.93 (m, 1H), 3.61-3.67 (m, 1H), 3.45-3.52 (m, 1H), 2.94-3.12 (m, 4H), 1.17 (d, J=6.4 Hz, 12H). MS (ESI) m/z 429.80 (M+H⁺).

Example 24

2-[2,6-(Diisopropyl)phenoxycarbonylamino]ethyl (2S)-2-amino-3-carboxypropionamide Trifluoroacetate Salt (35)

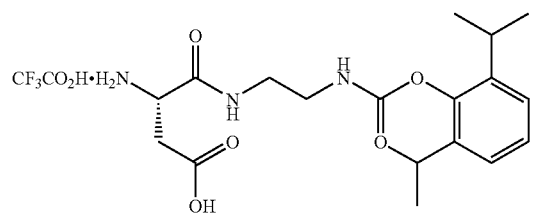

Following procedures for the preparation of compound (27) and first substituting 2-(tert-butoxycarbonylamino)ethylamine for Boc-glycinol in Step 1 of Example 19 and then substituting Boc-L-Asp(OᵗBu) for Boc-L-asparagine in Step 3 of Example 19 provided the title compound (35). ¹H-NMR (400 MHz, CD₃OD): δ 7.13 (m, 3H), 3.99 (dd, J=8.8, 4.4 Hz, 1H), 3.31-3.36 (m, 4H), 3.00-3.07 (m, 2H), 2.67-2.73 (dd, J=16.8, 5.2 Hz, 1H), 2.54-2.60 (dd, J=16.8, 9.6 Hz, 1H), 1.19 (d, J=6.8 Hz, 12H). MS (ESI) m/z 380.29 (M+H)⁺.

Example 25

2-[2,6-(Diisopropyl)phenoxycarbonylamino]ethyl (2S)-2-amino-3-hydroxypropionamide Hydrogen Formate Salt (36)

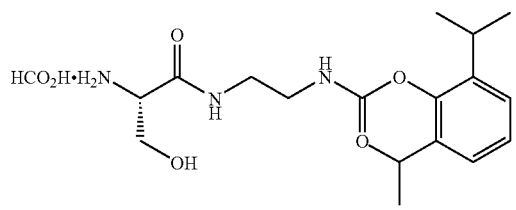

Following procedures for the preparation of compound (27) and first substituting 2-(tert-butoxycarbonylamino)ethylamine for Boc-glycinol in Step 1 of Example 19 and then substituting Boc-L-Ser(OᵗBu) for Boc-L-asparagine in Step 3 of Example 19 provided the title compound (36). ¹H-NMR (400 MHz, CD₃OD): δ 7.11-7.16 (m, 3H), 3.77-3.88 (m, 3H), 3.34-3.41 (m, 4H), 2.99-3.06 (m, 2H), 1.19 (d, J=6.8 Hz, 12H). MS (ESI) m/z 352.26 (M+H)⁺.

Example 26

2-[2,6-(Diisopropyl)phenoxycarbonylamino]ethyl (2S)-2-amino-3-methylbutanoylamide Hydrogen Formate Salt (37)

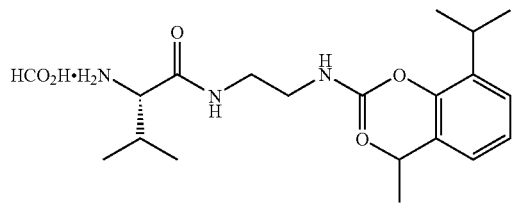

Following procedures for the preparation of compound (27) and first substituting 2-(tert-butoxycarbonylamino)

ethylamine for Boc-glycinol in Step 1 of Example 19 and then substituting Boc-L-valine for Boc-L-asparagine in Step 3 of Example 19 provided the title compound (37). $^1$H-NMR (400 MHz, CD$_3$OD): δ 7.13 (m, 3H), 3.29-3.34 (m, 5H), 3.00-3.04 (m, 2H), 2.14 (m, 1H), 1.19 (d, J=6.8 Hz, 12H), 1.04 (m, 6H). MS (ESI) m/z 364.30 (M+H)$^+$.

Example 27

2,6-(Diisopropyl)phenyl 4-[(2S)-2-amino-3-methyl-butyrlamino]butanoate Trifluoroacetate Salt (38)

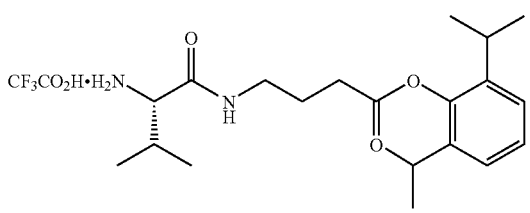

Step 1: 2,6-(Diisopropyl)phenyl 4-[(tert-butoxy)carbonylamino]butanoate (39)

To a homogeneous solution of Boc-γ-Amino butyric acid (1.015 g, 5.0 mmol), DMAP (60 mg, 0.5 mmol) and propofol (925 µL, 5.0 mmol) in toluene (15 mL) at room temperature was added dicyclohexylcarbodiimide (1.24 g, 6.0 mmol). The mixture was heated to 80° C. for 18 h. The reaction mixture was cooled to room temperature, the dicyclohexylurea was filtered off and the solution was diluted with ether (100 mL). The ether layer was washed with 10% citric acid (2×25 mL), saturated sodium bicarbonate (2×25 mL), and brine (2×25 mL). The organic layer was dried over MgSO$_4$ and then concentrated in vacuo The crude product (39) was used as such to the next step (1.45 g, 80% yield). MS (ESI) m/z 364.50 (M+H)$^+$.

Step 2: 2,6-(Diisopropyl)phenyl 4-aminobutanoate Trifluoroacetate Salt (40)

Compound (39) was treated with 30% TFA (3 mL) in dichloromethane (7 mL) for 30 min and the solvent removed in vacuo to afford the title compound (40).
$^1$H-NMR (400 MHz, CD$_3$OD): δ 7.14-7.19 (m, 3H), 3.03-3.07 (m, 2H), 2.81-2.90 (m, 4H), 2.04-2.08 (m, 2H), 1.17 (d, J=6.8 Hz, 12H). MS (ESI) m/z 264.50 (M+H)$^+$.

Step 3: 2,6-(Diisopropyl)phenyl 4-[(2S)-2-tert-butoxycarbonylamino-3-methylbutyrlamino}butanoate Trifluoroacetate Salt (41)

To a suspension of compound (40) (526 mL, 2 mmol) in DMF (2 mL) was added a homogeneous solution containing Boc-Val (434 mg, 2.0 mmol) diisopropylethylamine (0.75 mL, 4.4 mmol) and O-(1H-Benzotriazol-1-yl) N,N,N',N'-tetramethyluronium hexafluorophosphate (800 mg, 2.1 mmol) in DMF (2 ml). The resulting mixture was stirred at room temperature for 14 h and then diluted with 40 mL of ethyl acetate. The organic solution was washed with 10% aqueous citric acid solution (2×30 mL), saturated aqueous sodium bicarbonate solution (2×30 mL) and brine (2×30 mL). The organic layer was dried over magnesium sulfate and then concentrated in vacuo. The crude product (41) was used without further purification. MS (ESI) m/z 463.44 (M+H)$^+$.

Step 4: 2,6-(Diisopropyl)phenyl 4-[(2S)-2-amino-3-methylbutyrylamino]butanoate Trifluoroacetate Salt (38)

Compound (41) was treated with 30% TFA (3 mL) in dichloromethane (7 mL) for 30 min and the solvent removed in vacuo to afford the title compound (38). $^1$H-NMR (400 MHz, CD$_3$OD): δ 7.13-7.18 (m, 3H), 3.57 (d, J=6.4 Hz, 1H), 3.32-3.43 (m, 2H), 2.86-2.93 (m, 2H), 2.70-2.74 (m, 2H), 2.13-2.18 (m, 1H), 1.17 (d, J=6.8 Hz, 12H), 1.04-1.05 (m, 6H). MS (ESI) m/z 363.44 (M+H)$^+$.

Example 28

2,6-(Diisopropyl)phenyl 4-[(2S)-2-amino-3-carbamoylpropionylamino]butanoate Trifluoroacetate Salt (42)

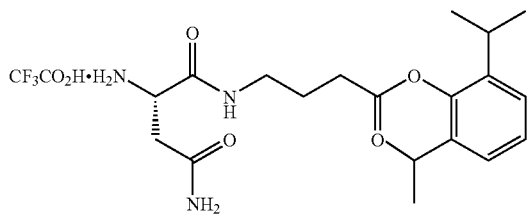

Following procedures for the preparation of compound (38) and substituting Boc-Asn for Boc-Val provided the title compound (42). $^1$H-NMR (400 MHz, CD$_3$OD): δ 7.13-7.20 (m, 3H), 4.05-4.08 (m, 1H), 3.36-3.37 (t, 2H), 2.86-2.93 (m, 2H), 2.85 (dd, J=4.4 Hz, 1H), 2.70-2.75 (m, 3H), 1.94-1.98 (m, 2H), 1.18 (d, J=7.2 Hz, 12H). MS (ESI) m/z 378.48 (M+H)$^+$.

Example 29

2,6-(Diisopropyl)phenyl 4-[(2S)-2-amino-4-carboxylbutyrylamino]butanoate Trifluoroacetate Salt (43)

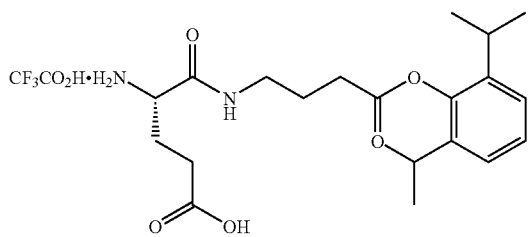

Following procedures for the reparation of compound (38) and substituting Boc-Glu(Otbu) for Boc-Val provided the title compound (43). $^1$H-NMR (400 MHz, CD$_3$OD): δ 7.13-7.17 (m, 3H), 3.80-3.84 (m, 1H), 3.33-3.38 (m, 2H), 2.88-2.91 (m, 2H), 2.70-2.74 (t, 2H), 2.40-2.43 (t, 2H), 1.96-2.07 (m, 2H), 1.18 (d, J=7.2 Hz, 12H). MS (ESI) m/z 393.49 (M+H)$^+$.

Example 30

2,6-(Diisopropyl)phenyl 4-[(2S)-2-amino-(3R)-3-hydroxylbutyryl]aminobutanoate Trifluoroacetate Salt (44)

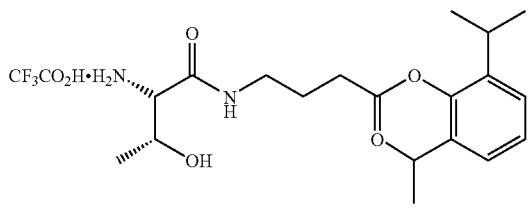

Following procedures for the preparation of compound (38) and substituting Boc-Thr(Otbu) for Boc-Val provided the title compound (44). $^1$H-NMR (400 MHz, CD$_3$OD): δ 7.12-7.20 (m, 3H), 3.98-4.05 (m, 1H), 3.59 (d, J=6.8 Hz, 1H), 3.31-3.41 (m, 2H), 2.86-2.92 (m, 2H), 2.71 (t, 2H), 1.946-2.019 (m, 2H), 1.2 (d, J=6.4 Hz, 3H), 1.18 (d, J=7.2 Hz, 12H). MS (ESI) m/z 365.33 (M+H)$^+$.

Example 31

2,6-(Diisopropyl)phenyl 4-[(2S)-pyrrolidin-2-ylcarbonylamino]butanoate Trifluoroacetate Salt (45)

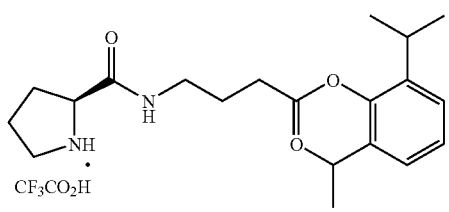

Following procedures for the preparation of compound (38) and substituting Boc-Pro for Boc-Val provided the title compound (45). $^1$H-NMR (400 MHz, CD$_3$OD): δ 7.12-7.20 (m, 3H), 4.23-4.25 (m, 1H), 3.33-3.40 (m, 4H), 2.86-2.92 (m, 2H), 2.71 (t, 2H), 2.41-2.43 (m, 1H), 1.18 (d, J=7.2 Hz, 12H). MS (ESI) m/z 361.50 (M+H)$^+$.

Example 32

2,6-(Diisopropyl)phenyl 4-[(2S)-2-amino-3-hydroxypropionylamino]butanoate Trifluoroacetate Salt (46)

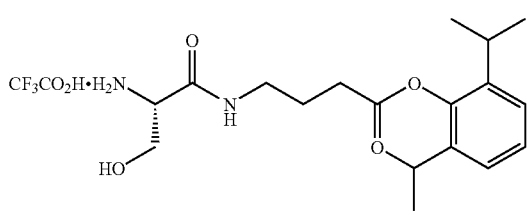

Following procedures for the preparation of compound (38) and substituting Boc-Ser(Otbu) for Boc-Val provided the title compound (46). $^1$H-NMR (400 MHz, CD$_3$OD): δ 7.12-7.20 (m, 3H), 3.78-3.92 (m, 3H), 3.33-3.40 (m, 3H), 2.86-2.92 (m, 2H), 2.75 (t, 2H), 1.93-2.01 (m, 2H), 1.18 (d, J=7.2 Hz, 12H). MS (ESI) m/z 351.45 (M+H)$^+$.

Example 33

Uptake of Propofol Following Oral Administration of Prodrugs to Monkeys

Step 1: Administration Protocol

Test compounds were administered by oral gavage or as an intravenous bolus injection to groups of two to four adult male Cynomologous (Macaca fascicularis) monkeys (weight approx 5 kg) as solutions in water or PEG400 at a dose of 25 mg-equivalents of propofol per kg body weight. Animals were fasted overnight before the study and for 4 hours post-dosing. Blood samples (1.0 mL) were obtained via the femoral vein at intervals over 24 hours after oral dosing. Blood was quenched immediately using acetonitrile with 1% formic acid and then was frozen at −80° C. until analyzed. Test compounds are administered in the monkeys with a minimum of 72 hour wash out period between dosing sessions.

Step 2: LC/MS/MS Analysis

Concentrations of propofol in plasma were determined using an API 4000 LC/MS/MS instrument equipped with an Agilent 1100 binary pump and an Agilent autosampler. The column was a Phenomenex Hydro-RP 4.6×50 mm column operating at room temperature. The mobile phases were (A) 2 mM aqueous ammonium acetate, and (B) 95% acetonitrile with 5 mM ammonium acetate. The gradient condition was: 5% B for 1 min, increasing to 90% B in 2.5 min and maintained for 2 min. 20 μL of sample was injected. A Turbo-IonSpray source was used, and propofol was detected in negative ion mode in Q1 at m/z=177. Prodrugs were detected in positive ion mode and peaks were integrated using Analyst 1.2 quantitation software.

Oral bioavailability (F) of propofol, resulting from oral administration of the propofol prodrugs (7), (29), the trifluoroacetate salt of (33) and the HCl salt of (33), in monkeys was determined by comparing the area under the propofol concentration vs time curve (AUC) following oral administration of a propofol prodrug with the AUC measured following intravenous administration of an equimolar dose of propofol itself. The above prodrugs provided greater than 10% absolute oral bioavailability of propofol, i.e., compared to the bioavailability of propofol following intravenous administration of an equimolar dose of propofol itself. Thus, prodrugs (7), (29), the trifluoroacetate salt of (33) and the HCl salt of (33) provided at least about 40 times higher oral bioavailability of propofol compared to the oral bioavailability of propofol itself. The results illustrate that prodrugs of the present disclosure can afford significant enhancements in oral bioavailability of propofol in monkeys.

Example 34

Uptake of Propofol Following Oral or Intravenous Administration of Prodrugs to Rats Step 1: Administration Protocol Propofol or propofol prodrug was administered as an intravenous bolus injection or by oral gavage to groups of four to six adult male Sprague-Dawley rats (weight approx 250 g). Animals were conscious at the time of the experiment. Propofol or propofol prodrug was orally administered as an aqueous solution at a dose equivalent to 25 mg of propofol per kg body weight. When administered intravenously, propofol or propofol prodrug was administered as a solution in Diprivan® (Astra-Zeneca) at a dose equivalent to 15 mg of propofol per kg body weight. Animals were fasted overnight before the study and for 4 hours post-dosing. Blood samples (0.3 mL) were obtained via a jugular vein cannula at intervals over 8 hours after oral dosing. Blood was quenched immediately using acetonitrile with 1% formic acid and then was frozen at −80° C. until analyzed.

Step 2: Sample Preparation for Absorbed Drug

1. In blank 1.5 mL tubes, 300 μL of 0.1% formic acid in acetonitrile was added.
2. Rat blood (300 μL) was collected at different times into EDTA tubes and vortexed to mix. A fixed volume of blood (100 μL) was immediately added into the Eppendorf tube and vortexed to mix.
3. Ten microliters of a propofol standard stock solution (0.04, 0.2, 1, 5, 25, 100 μg/mL) was added to 90 μL of blank rat blood quenched with 300 μL of 0.1% formic acid in acetonitrile. Then, 20 μL of p-chlorophenylalanine was added to each tube to make the to make up a final calibration standard (0.004, 0.02, 0.1, 0.5, 2.5, 10 μg/mL).
4. Samples were vortexed and centrifuged at 14,000 rpm for 10 min.
5. Supernatant was analyzed by LC/MS/MS.

Step 3: LC/MS/MS Analysis

An API 4000 LC/MS/MS spectrometer equipped with Agilent 1100 binary pumps and a CTC HTS-PAL autosampler were used in the analysis. A Phenomenex Synergihydro-RP 4.6×30 mm column was used during the analysis. The mobile phase for propofol analysis was (A) 2 mM ammonium acetate, and (B) 5 mM ammonium acetate in 95% acetonitrile. The mobile pahse for the analysis of propofol prodrugs was (A) 0.1% formic acid, and (B) 0.1% formic acid in acetonitrile. The gradient condition was: 10% B for 0.5 min, then to 95% B in 2.5 min, then maintained at 95% B for 1.5 min. The mobile phase was returned to 10% B for 2 min. An ACPI source was used on the API 4000. The analysis was done in negative ion mode for propofol and positive ion mode for propofol prodrugs. The MRM transition for each analyte was optimized using standard solutions. 5 μL of the samples were injected. Non-compartmental analysis was performed using WinNonlin (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$, (area under the serum concentration time curve from time zero to infinity, estimated using the log-linear trapezoidal method to the last collection time with extrapolation to infinity), and $t_{1/2,z}$ (terminal half-life).

The oral bioavailability (F) of propofol was determined by comparing the area under the propofol concentration vs time curve (AUC) following oral administration of propofol with the AUC of the propofol concentration vs time curve following intravenous administration of propofol on a dose normalized basis. Using this measurement technique, the oral bioavailability of propofol was found to be very low, as expected (F=0.23%).

Oral bioavailability (F) of propofol, resulting from oral administration of the propofol prodrug (38), in rats was determined by comparing the area under the propofol concentration vs time curve (AUC) following oral administration of the propofol prodrug (38), and with the AUC measured following intravenous administration of an equimolar dose of propofol itself. Prodrug (38) provided greater than 10% absolute oral bioavailability of propofol, i.e., compared to the bioavailability of propofol following intravenous administration of an equimolar dose of propofol itself. Thus, prodrug (38) provided at least about 40 times higher oral bioavailability of propofol compared to the oral bioavailability of propofol itself. The result illustrates that prodrugs of the present disclosure can afford significant enhancements in oral bioavailability of propofol in rats.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the claim(s) issuing herefrom. All publications and patents cited herein are incorporated by reference in their entirety.

What is claimed is:

1. A compound according to structural Formula (I):

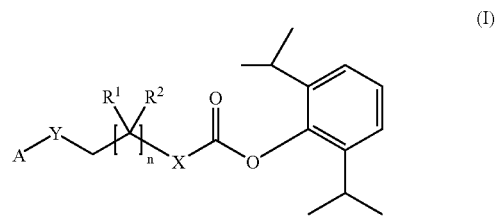

or pharmaceutically acceptable salts, hydrates, solvates or N-oxides thereof, wherein:

each $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, $R^1$ and $R^2$ together with the carbon atom to which they are bonded form a cycloalkyl, substituted cycloalkyl, cycloheteroalkyl or substituted cycloheteroalkyl ring;

A is hydrogen, acyl, substituted acyl, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl or optionally, A, Y and one of $R^1$ and $R^2$ together with the atoms to which they are bonded form a cycloheteroalkyl or substituted cycloheteroalkyl ring;

Y is —O— or —NR$^3$—;

$R^3$ is hydrogen, alkyl, substituted alkyl, arylalkyl or substituted arylalkyl;

n is an integer from 1 to 5;

X is —NR$^4$—, —O—, —CH$_2$— or —S—; and $R^4$ is hydrogen, alkyl, substituted alkyl, arylalkyl or substituted arylalkyl.

2. The compound of claim 1, wherein X is —O—, —NH— or —CH$_2$—.

3. The compound of claim 1, wherein Y is —O— or —NH—.

4. The compound of claim 1, wherein X is —O— and Y is —NH— or —O—.

5. The compound of claim 1, wherein X is —O—, —NH— or —CH$_2$—, and Y is —NH—.

6. The compound of claim 1, wherein n is 1.

7. The compound of claim 1, wherein n is 2.

8. The compound of claim 1, wherein A is hydrogen or [H$_2$NCHR$^5$C(O)]—, and R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring.

9. The compound of claim 1, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl.

10. The compound of claim 1, wherein A is hydrogen or [H$_2$NCHR$^5$C(O)]—, and R$^5$ is hydrogen, methyl, isopropyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$(CH$_2$)$_3$NH$_2$, 4-hydroxybenzyl, 3-indolylmethyl or R$^5$ and the alpha amino group together with the atoms to which they are bonded form a pyrrolidine ring.

11. The compound of claim 1, wherein each R$^1$ and R$^2$ is independently hydrogen, C$_{1-6}$ alkyl, substituted C$_{1-6}$ alkyl, or optionally, R$^1$ and R$^2$ together with the carbon atom to which they are bonded form a C$_{5-7}$ cycloalkyl or substituted C$_{5-7}$ cycloalkyl ring.

12. The compound of any one of claims 1, 7 and 11, wherein the substituent is halogen, —NH$_2$, —OH, —CN, —COOH, —C(O)NH$_2$, —C(O)OR$^7$ or —NR$^7_3{}^+$, and each R$^7$ is independently C$_{1-3}$ alkyl.

13. The compound of claim 1, wherein n is 1, and R$^1$ and R$^2$ are each hydrogen, each methyl or optionally, R$^1$ and R$^2$ together with the carbon atom to which they are bonded form a cyclohexyl ring.

14. The compound of claim 1, wherein n is 1, Y is —O— or —NH—, X is —O—, —NH— or —CH$_2$—, R$^1$ and R$^2$ are each hydrogen, each methyl or R$^1$ and R$^2$ together with the carbon atom to which they are bonded form a cyclohexyl ring, and A is hydrogen or [H$_2$NCHR$^5$C(O)]—, wherein R$^5$ is hydrogen, methyl, isopropyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$(CH$_2$)$_3$NH$_2$, 4-hydroxybenzyl, 3-indolylmethyl or R$^5$ and the alpha amino group together with the atoms to which they are bonded form a pyrrolidine ring.

15. A compound according to structural Formula (II):

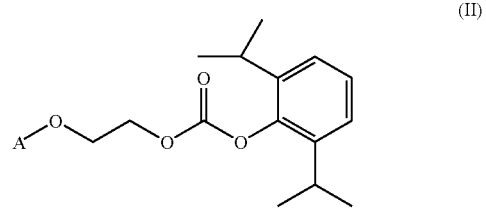

(II)

or pharmaceutically acceptable salts, hydrates, solvates or N-oxides thereof, wherein:

A is hydrogen or [H$_2$NCHR$^5$C(O)]— and R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring.

16. The compound of claim 15, wherein the substituent is halogen, —NH$_2$, —OH, —CN, —COOH, —C(O)NH$_2$, —C(O)OR$^7$ or —NR$^7_3{}^+$ and each R$^7$ is independently C$_{1-3}$ alkyl.

17. The compound of claim 15, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)N—H$_2$, phenyl, benzyl, 4-hydroxybenzyl, 4-imidazolylmethyl or 3-indolylmethyl.

18. The compound of claim 15, wherein A is hydrogen or [H$_2$NCHR$^5$C(O)]— and R$^5$ is —CH$_2$OH or —CH$_2$CONH$_2$.

19. A compound according to structural Formula (III):

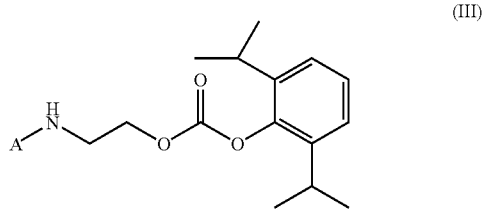

(III)

or pharmaceutically acceptable salts, hydrates, solvates or N-oxides thereof, wherein:

A is hydrogen, [H$_2$NCHR$^5$C(O)]— or —C(O)OR$^6$;

R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring; and R$^6$ is hydrogen, C$_{1-6}$ alkyl, substituted C$_{1-6}$ alkyl, C$_{5-7}$ aryl, substituted C$_{5-7}$ aryl, C$_{6-8}$ arylalkyl or substituted C$_{6-8}$ arylalkyl.

20. The compound of claim 19, wherein the substituent is halogen, —NH$_2$, —OH, —CN, —COOH, —C(O)NH$_2$, —C(O)OR$^7$ or —NR$^7_3{}^+$ and each R$^7$ is independently C$_{1-3}$ alkyl.

21. The compound of claim 19, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl.

22. The compound of claim 19, wherein A is hydrogen or [H$_2$NCHR$^5$C(O)]— and R$^5$ is hydrogen, isopropyl, —CH$_2$OH, —CH$_2$CONH$_2$, —CH$_2$(CH$_2$)$_3$NH$_2$ or 4-hydroxybenzyl.

23. A compound of structural Formula (IV):

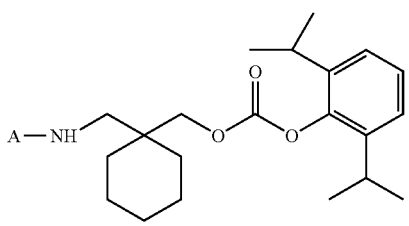

(IV)

or pharmaceutically acceptable salts, hydrates, solvates or N-oxides thereof, wherein:

A is hydrogen or [H$_2$NCHR$^5$C(O)]— and R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring.

24. The compound of claim 23, wherein the substituent is halogen, —NH$_2$, —OH, —CN, —COOH, —C(O)NH$_2$, —C(O)OR$^7$ or —NR$^7_3{}^+$ and each R$^7$ is independent C$_{1-3}$ alkyl.

25. The compound of claim 23, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl.

26. The compound of claim 23, wherein A is [H$_2$NCHR$^5$C(O)]— and R$^5$ is isopropyl, —CH$_2$OH or —CH(OH)CH$_3$.

27. A compound according to structural Formula (V):

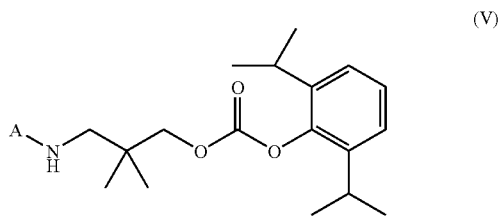

(V)

or pharmaceutically acceptable salts, hydrates, solvates or N-oxides thereof, wherein:

A is hydrogen or [H$_2$NCHR$^5$C(O)]— and R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring.

28. The compound of claim 27, wherein the substituent is halogen, —NH$_2$, —OH, —CN, —COOH, —C(O)NH$_2$, —C(O)OR$^7$ or —NR$^7_3{}^+$ and each R$^7$ is independently C$_{1-3}$ alkyl.

29. The compound of claim 27, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl 3-indolylmethyl or R$^5$ and the alpha amino group together with the atoms to which they are bonded form a pyrrolidine ring.

30. The compound of claim 27, wherein A is [H$_2$NCHR$^5$C(O)]— and R$^5$ is hydrogen, methyl, isopropyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$(CH$_2$)$_3$NH$_2$, 4-hydroxybenzyl, or R$^5$ and the alpha amino group together with the atoms to which they are bonded form a pyrrolidine ring.

31. A compound of structural Formula (XII):

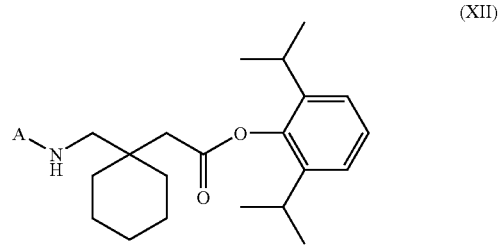

(XII)

or pharmaceutically acceptable salts, hydrates, solvates or N-oxides thereof, wherein:

A is hydrogen or [H$_2$NCHR$^5$C(O)]— and R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{-5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring.

32. The compound of claim 31, wherein the substituent is halogen, —NH$_2$, —OH, —CN, —COOH, —C(O)NH$_2$, —C(O)OR$^7$ or —NR$^7_3{}^+$ and each R$^7$ is independently C$_{1-3}$ alkyl.

33. The compound of claim 31, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl or 3-indolylmethyl.

34. The compound of claim 31, wherein A is [H$_2$NCHR$^5$C(O)]— and R$^5$ is isopropyl, —CH$_2$OH or —CH(OH)CH$_3$.

35. A compound according to structural Formula (XIII):

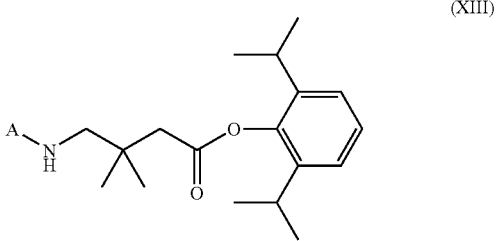

(XIII)

or pharmaceutically acceptable salts, hydrates, solvates or N-oxides thereof, wherein:

A is hydrogen or [H$_2$NCHR$^5$C(O)]— and R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring.

36. The compound of claim 35, wherein the substituent is halogen, —NH$_2$, —OH, —CN, —COOH, —C(O)NH$_2$, —C(O)OR$^7$ or —NR$^7_3{}^+$ and each R$^7$ is independently C$_{1-3}$ alkyl.

37. The compound of claim 35, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl 3-indolylmethyl or R$^5$ and the alpha amino group together with the atoms to which they are bonded form a pyrrolidine ring.

38. The compound of claim 35, wherein A is [H$_2$NCHR$^5$C(O)]— and R$^5$ is hydrogen, methyl, isopropyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$(CH$_2$)$_3$NH$_2$, 4-hydroxybenzyl, or R$^5$ and the alpha amino group together with the atoms to which they are bonded form a pyrrolidine ring.

39. A compound according to structural Formula (XIV):

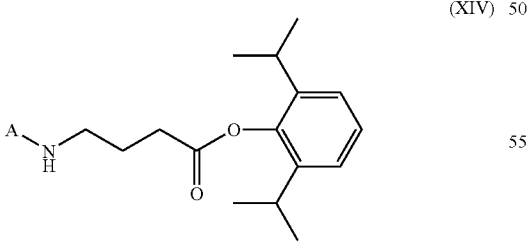

(XIV)

or pharmaceutically acceptable salts, hydrates, solvates or N-oxides thereof, wherein:

A is hydrogen or [H$_2$NCHR$^5$C(O)]— and R$^5$ is hydrogen, C$_{1-6}$ alkyl, substituted C$_{1-6}$ alkyl, C$_{5-7}$ aryl, substituted C$_{5-7}$ aryl, C$_{6-11}$ arylalkyl, substituted C$_{6-11}$ arylalkyl, C$_{1-6}$ heteroalkyl, substituted C$_{1-6}$ heteroalkyl, C$_{5-7}$ heteroaryl, substituted C$_{5-7}$ heteroaryl, C$_{6-11}$ heteroarylalkyl, substituted C$_{6-11}$ heteroarylalkyl or optionally, R$^5$ and the alpha amino group together with the atoms to which they are bonded form a C$_{5-7}$ cycloheteroalkyl or substituted C$_{5-7}$ cycloheteroalkyl ring.

40. The compound of claim 39, wherein the substituent is halogen, —NH$_2$, —OH, —CN, —COOH, —C(O)NH$_2$, —C(O)OR$^7$ or —NR$^7_3{}^+$ and each R$^7$ is independently C$_{1-3}$alkyl.

41. The compound of claim 39, wherein A is hydrogen or [H$_2$NCHR$^5$C(O)]— and R$^5$ is hydrogen, methyl, isopropyl, isobutyl, sec-butyl, tert-butyl, cyclopentyl, cyclohexyl, —CH$_2$OH, —CH(OH)CH$_3$, —CH$_2$NH$_2$, —CH$_2$CO$_2$H, —CH$_2$CH$_2$CO$_2$H, —CH$_2$CONH$_2$, —CH$_2$CH$_2$CONH$_2$, —CH$_2$CH$_2$SCH$_3$, —CH$_2$SH, —CH$_2$(CH$_2$)$_3$NH$_2$, —CH$_2$CH$_2$CH$_2$NHC(NH)NH$_2$, phenyl, benzyl, 4-hydroxybenzyl, 4-imidazolylmethyl 3-indolylmethyl or R$^5$ and the alpha amino group together with the atoms to which they are bonded form a pyrrolidine ring.

42. The compound of claim 39, wherein A is [H$_2$NCHR$^5$C(O)]— and R$^5$ is —CH$_2$OH, —CH(OH)CH$_3$, —CH$_2$CH$_2$CO$_2$H, —CH$_2$CONH$_2$ or R$^5$ and the alpha amino group together with the atoms to which they are bonded form a pyrrolidine ring.

43. A compound selected from:
- 2,6-(Diisopropyl)phenyl 1-[((2S)-2-amino-3-methylbutyryl)aminomethyl]-1-cyclohexane acetate;
- 2,6-(Diisopropyl)phenyl 1-[((2S)-2-amino-3-hydroxypropionyl)aminomethyl]-1-cyclohexane acetate;
- 2,6-(Diisopropyl)phenyl 1-[((2S)-2-amino-(3R)-3-hydroxybutyryl)aminomethyl]-1-cyclohexane acetate;
- 2,6-(Diisopropyl)phenyl 4-[(2S)-2-amino-3-carbamoylpropionylamino]-3,3-dimethylbutanoate;
- 2,6-(Diisopropyl)phenyl 4-[(2S)-2-amino-3-carboxypropionylamino]-3,3-dimethylbutanoate;
- 2,6-(Diisopropyl)phenyl 4-[(2S)-2,3-diaminopropionylamino]-3,3-dimethylbutanoate;
- 2,6-(Diisopropyl)phenyl 4-[(2S)-2-amino-3-hydroxypropionylamino]-3,3-dimethylbutanoate;
- 2,6-(Diisopropyl)phenyl 4-[(2S)-2-aminopropionylamino]-3,3-dimethylbutanoate;
- 2,6-(Diisopropyl)phenyl 4-[(2S)-2-amino-(3R)-3-hydroxybutyryl]amino-3,3-dimethylbutanoate;
- 2,6-(Diisopropyl)phenyl 4-[(2S)-2-amino-(4-hydroxyphenyl)propionylamino]-3,3-dimethylbutanoate;
- 2,6-(Diisopropyl)phenyl 4-[(2S)-2-amino-(indol-3-yl)propionylamino]-3,3-dimethylbutanoate;
- 2,6-(Diisopropyl)phenyl 4-[aminomethylcarbonylamino]-3,3-dimethylbutanoate;
- 2,6-(Diisopropyl)phenyl 4-[(2S)-2-amino-4-carboxybutyrylamino]-3,3-dimethylbutanoate;
- 2,6-(Diisopropyl)phenyl 4-[(2S)-2,6-diaminohexanoylamino]-3,3-dimethylbutanoate;
- 2,6-(Diisopropyl)phenyl 4-[(2S)-pyrrolidin-2-ylcarbonylamino]-3,3-dimethylbutanoate;
- 2,6-(Diisopropyl)phenyl 4-[(2S)-2-amino-3-methylbutyrylamino]-3,3-dimethylbutanoate;
- 2-[2,6-(Diisopropyl)phenoxycarbonyloxy]ethyl (2S)-2-amino-3-carbamoylpropionate;
- 2-[2,6-(Diisopropyl)phenoxycarbonyloxy]ethanol;
- 2-[2,6-(Diisopropyl)phenoxycarbonyloxy]ethyl (2S)-2-amino-3-hydroxypropionate;
- 2-[2,6-(Diisopropyl)phenoxycarbonyloxy]ethyl (2S)-2-amino-3-carbamoylpropionamide;
- 1-Amino-2-[2,6-(diisopropyl)phenoxycarbonyloxy]ethane;
- 2-[2,6-(Diisopropyl)phenoxycarbonyloxy]ethyl glycinamide;

2-[2,6-(Diisopropyl)phenoxycarbonyloxy]ethyl (2S)-2,6-diaminohexanoylamide;
2-[2,6-(Diisopropyl)phenoxycarbonyloxy]ethyl (2S)-2-amino-3-hydroxypropionamide;
2-[2,6-(Diisopropyl)phenoxycarbonyloxy]ethyl (2S)-2-amino-(4-hydroxyphenyl)propionamide;
2-[2,6-(Diisopropyl)phenoxycarbonylamino]ethyl (2S)-2-amino-3-carboxypropionamide;
2-[2,6-(Diisopropyl)phenoxycarbonylamino]ethyl (2S)-2-amino-3-hydroxypropionamide;
2-[2,6-(Diisopropyl)phenoxycarbonylamino]ethyl (2S)-2-amino-3-methylbutanoylamide;
2,6-(Diisopropyl)phenyl 4-[(2S)-2-amino-3-methylbutyrylamino]butanoate;
2,6-(Diisopropyl)phenyl 4-[(2S)-2-amino-3-carbamoylpropionylamino]butanoate;
2,6-(Diisopropyl)phenyl 4-[(2S)-2-amino-4-carboxybutyrylamino]butanoate;
2,6-(Diisopropyl)phenyl 4-[(2S)-2-amino-(3R)-3-hydroxylbutyryl]aminobutanoate; and
2,6-(Diisopropyl)phenyl 4-[(2S)-pyrrolidin-2-ylcarbonylamino]butanoate;
2,6-(Diisopropyl)phenyl 4-[(2S)-2-amino-3-hydroxypropionylamino]butanoate;
or pharmaceutically acceptable salts, hydrates, solvates or N-oxides thereof.

44. A compound selected from:
2,6-(Diisopropyl)phenyl 1-[((2S)-2-amino-(3R)-3-hydroxybutyryl)aminomethyl]-1-cyclohexane acetate;
1-Amino-2-[2,6-(diisopropyl)phenoxycarbonyloxy]ethane;
2-[2,6-(Diisopropyl)phenoxycarbonyloxy]ethyl (2S)-2-amino-3-hydroxypropionamide; and
2,6-(Diisopropyl)phenyl 4-[(2S)-2-amino-3-methylbutyrylamino]butanoate;
or pharmaceutically acceptable salts, hydrates, solvates or N-oxides thereof.

45. A pharmaceutical composition comprising a therapeutically effective amount of a compound according to claim 1 and a pharmaceutically acceptable vehicle.

46. The composition of claim 45 for treatment of nausea and vomiting, comprising a 5-HT$_3$ antagonist.

47. The composition of claim 46, wherein the 5-HT$_3$ antagonist is selected from the group consisting of ondansetron, granisetron, dolasetron, and palonosetron.

48. The composition of claim 45 for treatment of nausea and vomiting, comprising a corticosteroid.

49. The composition of claim 48, wherein the corticosteroid comprises dexamethasone.

* * * * *